United States Patent [19]

Hamon

[11] Patent Number: 5,098,932
[45] Date of Patent: Mar. 24, 1992

[54] CYCLIC ETHER DERIVATIVES
[75] Inventor: Annie Hamon, Reims, France
[73] Assignee: Imperial Chemical Industries PLC, ICI Pharma, Reims Cedex, France
[21] Appl. No.: 454,911
[22] Filed: Dec. 22, 1989
[30] Foreign Application Priority Data
   Dec. 23, 1988 [EP] European Pat. Off. ......... 884033119
[51] Int. Cl.$^5$ ................. A61K 31/335; C07D 317/22
[52] U.S. Cl. ...................... 514/462; 514/467; 549/454; 549/453; 549/452; 549/451; 549/449; 549/342; 549/341
[58] Field of Search ............... 549/449, 451, 453, 454, 549/452, 341, 342; 514/462, 467
[56] References Cited
   U.S. PATENT DOCUMENTS

| | | | |
|---|---|---|---|
| 3,661,917 | 5/1972 | Kaiser et al. | 514/314 |
| 3,743,737 | 7/1973 | Kaiser et al. | 514/314 |
| 4,876,346 | 10/1989 | Musser | 546/172 |
| 4,918,081 | 4/1990 | Huang | 514/311 |
| 4,920,130 | 4/1990 | Huang | 514/311 |
| 4,920,131 | 4/1990 | Huang | 514/311 |
| 4,920,132 | 4/1990 | Huang | 514/314 |
| 4,920,133 | 4/1990 | Huang | 514/314 |

FOREIGN PATENT DOCUMENTS

| | | |
|---|---|---|
| 0110405 | 6/1984 | European Pat. Off. . |
| 0181568 | 5/1986 | European Pat. Off. . |
| 0190722 | 8/1986 | European Pat. Off. . |
| 0200101 | 12/1986 | European Pat. Off. . |
| 0271287 | 6/1988 | European Pat. Off. . |
| 0349062 | 1/1990 | European Pat. Off. . |

Primary Examiner—Nicky Chan
Attorney, Agent, or Firm—Cushman, Darby & Cushman

[57] ABSTRACT

The invention concerns a cyclic ether derivative of the formula I, $$Ar^1-A^1-O-Ar^2-\underset{R^3}{\underset{|}{\overset{OR^1}{\overset{|}{C}}}}-R^2 \qquad I$$

wherein
$Ar^1$ is optionally substituted phenyl or naphthyl;
$A^1$ is (1-6C)alkylene, (3-6C)alkenylene, (3-6C)alkynylene or cyclo(3-6C)alkylene;
$Ar^2$ is optionally substituted phenylene, or a 6 membered heterocyclene moiety containing up to three nitrogen atoms;
$R^1$ and $R^2$ together form a group of the formula $-A^2-X-A^3-$ wherein each of $A^2$ and $A^3$ is (1-6C)alkylene and X is oxy, thio, sulphinyl, sulphonyl or imino; and
$R^3$ is (1-6C)alkyl, (2-6C)alkenyl, (2-6C)alkynyl or substituted (1-4C)alkyl;
or a pharmaceutically-acceptable salt thereof.

The compounds of the invention are inhibitors of the enzyme 5-lipoxygenase.

9 Claims, No Drawings

CYCLIC ETHER DERIVATIVES

This invention concerns novel cyclic ether derivatives and more particularly novel cyclic ether derivatives which are inhibitors of the enzyme 5-lipoxygenase (hereinafter referred to as 5-LO). The invention also concerns processes for the manufacture of said cyclic ether derivatives and novel pharmaceutical compositions containing said cyclic ether derivatives. Also included in the invention is the use of said cyclic ether derivatives in the treatment of various inflammatory and/or allergic diseases in which the direct or indirect products of 5-LO catalysed oxidation of arachidonic acid are involved, and the production of new medicaments for such use.

As stated above the cyclic ether derivatives described hereinafter are-inhibitors of 5-LO, which enzyme Is known to be involved in catalysing the oxidation of arachidonic acid to give rise via a cascade process to the physiologically active leukotrienes such as leukotriene $B_4$ (LTB$_4$) and the peptido-lipid leukotrienes such as leukotriene $C_4$ (LTC$_4$) and leukotriene $D_4$ (LTD$_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain cyclic ether derivatives are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a cyclic ether derivative of the formula I (set out hereinafter) wherein Ar$^1$ is phenyl or naphthyl which may optionally bear one or more substituentsselected from halogeno, hydroxy, carboxy, cyano, (1–4C)alkyl, (2–4C)alkenyl, (2–4C)alkynyl, (1–4C)alkoxy, (1–4C)alkylthio, (1–4C-)alkylsulphinyl, (1–4C)alkylsulphonyl, (1–4C)alkylamino, di-[(1–4C)alkyl]amino, (1–4C)alkoxycarbonyl, (2–4C)alkanoyl, hydroxy-(1–4C)alkyl, fluoro-(1–4C)alkyl and cyano-(1–4C)alkoxy;

wherein A$^1$ is (1–6C)alkylene, (3–6C)alkenylene, (3–6C)alkynylene or cyclo(3–6C)alkylene;

wherein Ar$^2$ is phenylene which may optionally bear one or two substituents selected from halogeno, hydroxy, amino, nitro, cyano, carbamoyl, (1–4C)alkyl, (3–4C)alkenyloxy, (1–4C)alkoxy, (1–4C)alkylthio, (1–4C)alkylsulphinyl, (1–4C)alkylsulphonyl, (1–4C)alkylamino, di-[(1–4C)alkyl]amino, fluoro-(1–4C)alkyl, (1–4C)alkoxycarbonyl, N-[(1–4C)alkyl]carbamoyl, N,N-di-[(1–4C)alkylcarbamoyl, (2–4C)alkanoylamino, cyano-(1–4C)alkoxy, carbamoyl-(1–4C)alkoxy and (1–4C)alkoxycarbonyl-(1–4C)alkoxy; or Ar$^2$ is a 6-membered heterocyclene moiety containing up to three nitrogen atoms;

wherein R$^1$ and R$^2$ together form a group of the formula —A$^2$—X—A$^3$— which, together with the oxygen atom to which A$^2$ is attached and with the carbon atom to which A$^3$ is attached, defines a ring having 5 to 7 ring atoms, wherein A$^2$ and A$^3$, which may be the same or different, each is (1–6C)alkylene and X is oxy, thio, sulphinyl, sulphonyl or imino, and which ring may bear one or two substituents, which may be the same or different, selected from hydroxy, (1–4C)alkoxy, hydroxy(1–4C)alkyl and (1–4C)alkoxy-(1–4C)alkyl; and wherein R$^3$ is (1–6C)alkyl, (2–6C)alkenyl, (2–6C)alkynyl, fluoro-(1–4C)alkyl, cyano-(1–4C)alkyl, hydroxy-(1–4C)alkyl, (1–4C)alkoxy-(1–4C)alkyl, (2–4C)alkanoyloxy(1–4C)alkyl or (2–4C)alkanoyl-(1–4C)alkyl; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more substituents containing an asymmetric carbon atom, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for a halogeno substituent which may be present on Ar$^1$ or Ar$^2$ is, for example, fluoro, chloro, bromo or iodo.

A suitable value for a (1–4C)alkyl substituent which may be present on Ar$^1$ or Ar$^2$ is, for example, methyl, ethyl, propyl, isopropyl, butyl, isobutyl, sec-butyl or tert-butyl.

A suitable value for a (2–4C)alkenyl substituent on Ar$^1$ is, for example, vinyl, allyl, 2-butenyl or 3-butenyl.

A suitable value or a (2–4C)alkynyl substituent on Ar$^1$ is, for example, ethynyl, 1-propynyl, 2-propynyl, 1-butynyl or 2-butynyl.

A suitable value for a (1–4C)alkoxy substituent which may be present on Ar$^1$ or Ar$^2$ is, for example, methoxy, ethoxy, propoxy, isopropoxy or butoxy.

A suitable value for a (2–4C)alkanoyl substituent which may be present on Ar$^1$ is, for example, acetyl, propionyl or butyryl. A suitable value for a hydroxy-(1–4C)alkyl substituent which may be present on Ar$^1$ is, for example, hydroxymethyl, 1-hydroxyethyl, 2-hydroxyethyl, 1-hydroxypropyl, 2-hydroxypropyl or 3-hydroxypropyl.

Suitable values for substituents which may be present on $Ar^1$ include, for example:

for (1–4C)alkylthio: methylthio, ethylthio, propylthio, isopropylthio and butylthio;

for (1–4C)alkylsulphinyl: methylsulphinyl, ethylsulphinyl, propylsulphinyl, isopropylsulphinyl and butylsulphinyl;

for (1–4C)alkylsulphonyl: methylsulphonyl, ethylsulphonyl, propylsulphonyl, isopropylsulphonyl and butylsulphonyl;

for (1–4C)alkylamino: methylamino, ethylamino, propylamino and butylamino;

for di-[(1–4C)alkyl]amino: dimethylamino, diethylamino and dipropylamino;

for (1–4C)alkoxycarbonyl: methoxycarbonyl, ethoxycarbonyl and tert-butoxycarbonyl;

for fluoro-(1–4C)alkyl: fluoromethyl, difluoromethyl, trifluoromethyl, 2-fluoroethyl, 2,2,2-trifluoroethyl and pentafluoroethyl.

A suitable value for the number of substituents which may be present on $Ar^1$ is, for example, one, two or three.

A suitable value for $A^1$ when it is (1–6C)alkylene is, for example, methylene, ethylene, ethylidene, trimethylene, propylidene, tetramethylene or pentamethylene; when it is (3–6C)alkenylene is, for example, 1-propenylene, 2-methylprop-1-enylene, 3-methylprop-1-enylene, 1-butenylene or 2-butenylene; and when it is (3–6C)alkynylene is, for example, 1-propynylene, 3-methylprop-1-ynylene, 1-butynylene or 2-butynylene.

A suitable value for $A^1$ when it is cyclo(3–6C)alkylene is, for example, cyclopropylidene, 1-2-cyclopropylene, cyclopentylidene, 1,2-cyclopentylene, cyclohexylidene or 1,4-cyclohexylene.

A suitable value for $Ar^2$ when it is phenylene is, for example, 1,3-phenylene or 1,4-phenylene.

A suitable value for $Ar^2$ when it is a 6-membered heterocyclene moiety containing up to three nitrogen atoms is, for example, pyridylene, pyrimidinylene, pyridazinylene, pyrazinylene or 1,3,5-triazinylene. Conveniently $Ar^2$ when it is a 6-membered heterocyclene moiety containing up to three nitrogen atoms is, for example, 2,4-, 2,5-, 3,5- or 2,6-pyridylene, 2,4-, 2,5 or 4,6-pyrimidinylene, 3,5- or 3,6-pyridazinylene or 2,5- or 2,6-pyrazinylene.

Suitable values for substituents which may be present on $Ar^2$ include, for example:

for (3–4C)alkenyloxy: allyloxy, methylallyoxy, but-2-enyloxy and but-3-enyloxy;

for N-[(1–4C)alkylcarbamoyl: N-methylcarbamoyl, N-ethylcarbamoyl and N-propylcarbamoyl;

for N,N-di-[(1–4C)alkyl]-carbamoyl: N,N-dimethylcarbamoyl and N,N-diethylcarbamoyl;

for (2–4C)alkanoylamino: acetamido, propionamido and butyramido;

for cyano-(1–4C)alkoxy: cyanomethoxy, 2-cyanoethoxy and 3-cyanopropoxy;

for carbamoyl-(1–4C)alkoxy: carbamoylmethoxy, 2-carbamoylethoxy and 3-carbamoylpropoxy;

for (1–4C)alkoxycarbonyl-(1–4C)-alkoxy: methoxycarbonylmethoxy, 2-methoxycarbonylethoxy, ethoxycarbonylmethoxy and 2-ethoxycarbonylethoxy.

A suitable value for $R^3$ when it is (1–6C)alkyl is, for example, methyl, ethyl, propyl, butyl, pentyl or hexyl.

A suitable value for $R^3$ when it is (2–6C)alkenyl is for example, vinyl, allyl, 2-butenyl or 3-butenyl; and when it is (2–6C)alkynyl is, for example, ethynyl, 1-propynyl, 2-propynyl, 1-butynyl or 2-butynyl.

A suitable value for $R^3$ when it is cyano-(1–4C)alkyl is, for example, cyanomethyl, 2-cyanoethyl or 3-cyanopropyl; when it is fluoro-(1–4C)alkyl is, for example, fluoromethyl, difluoromethyl, trifluoromethyl, 2-fluoroethyl, 2,2,2-trifluoroethyl or pentafluoroethyl; when it is hydroxy-(1–4C)alkyl is, for example, hydroxymethyl, 1-hydroxyethyl, 2-hydroxyethyl, 1-hydroxypropyl, 2-hydroxypropyl or 3-hydroxypropyl; when it is (1–4C)alkoxy-(1–4C)alkyl is, for example, methoxymethyl, 1-methoxyethyl, 2-methoxyethyl, 1-methoxypropyl, 2-methoxypropyl, 3-methoxypropyl, ethyoxymethyl, 1-ethoxyethyl, 2-ethoxyethyl, 1-ethoxypropyl, 2-ethoxypropyl or 3-ethoxypropyl; when it is (2–4C)alkanoyloxy-(1–4C)alkyl is, for example, acetoxymethyl, 2-acetoxyethyl, 3-acetoxypropyl, propionyloxymethyl, 2-propionyloxyethyl or 3-propionyloxypropyl and when it is (2–4C)alkanoyl-(1–4C)alkyl is, for example, acetonyl, 2-acetylethyl, 3-acetylpropyl or propionylmethyl.

When $R^1$ and $R^2$ together form a group of the formula $—A^2—X—A^3—$ which together with the oxygen atom to which $A^2$ is attached and with the carbon atom to which $A^3$ is attached, defines a ring having 5 to 7 ring atoms then a suitable value for $A^2$ or $A^3$, which may be the same or different, when each is (1–6C)alkylene is, for example, methylene, ethylene, ethylidene, trimethylene, propylidene, isopropylidene, butylidene, isobutylidene, isopentylidene, sec-butylidene, pentan-2-ylidene, pentan-3-ylidene, hexan-2-ylidene, cyclopentylidene or cyclohexylidene.

Suitable values for the one or two substituents which may be present on said 5- to 7-membered ring include, for example:

for (1–4C)alkoxy: methoxy, ethoxy, propoxy, isopropoxy and butoxy;

for hydroxy-(1–4C)alkyl: hydroxymethyl, 2-hydroxyethyl and 3-hydroxypropyl;

for (1–4C)alkoxy-(1–4C)alkyl: methoxymethyl, 2-methoxyethyl, 3-methoxypropyl, ethoxymethyl and 2-ethoxyethyl.

A suitable pharmaceutically-acceptable salt of a cyclic derivative of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a cyclic ether derivative of the invention which is sufficiently acidic (for example a cyclic ether derivative of the invention which contains a carboxy group) is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, cyclic ether derivatives of the formula I wherein:

(a) $Ar^1$ is phenyl, naphth-1-yl or naphth-2-yl which may optionally bear one, two or three substituents selected from fluoro, chloro, bromo, iodo, cyano, methyl, methoxy, methylthio, methylsulphinyl, methylsulphonyl, methoxycarbonyl, difluoromethyl and trifluoromethyl; and $A^1$, $Ar^2$, $R^1$, $R^2$ and $R^3$ have any of the meanings defined hereinbefore;

(b) $Ar^1$ is phenyl or naphth-2-yl which may optionally bear one or two substituents selected from fluoro, chloro, bromo, cyano, methyl, ethyl, propyl, butyl, isobutyl, tert-butyl, difluoromethyl, trifluoromethyl and cyanomethoxy; and $A^1$, $Ar^2$, $R^1$, $R^2$ and $R^3$ have any of the meanings defined hereinbefore;

(c) $A^1$ is methylene, ethylene, trimethylene, 1-propenylene, 2-methylprop-1-enylene or 1-propynylene; and $Ar^1$, $Ar^2$, $R^1$, $R^2$ and $R^3$ have any of the meanings defined hereinbefore;

(d) $A^1$ is methylene, 1-propenylene or 1-propynylene; and $Ar^1$, $Ar^2$, $R^1$, $R^2$ and $R^3$ have any of the meanings defined hereinbefore;

(e) $Ar^2$ is 1,3-phenylene or 1,4-phenylene which may optionally bear one substituent selected from chloro, bromo, hydroxy, amino, nitro, methyl, methoxy, allyloxy, methylthio, methylsulphinyl, methylsulphonyl, methylamino, dimethylamino, trifluoromethyl, acetamido, cyanomethoxy and carbamoylmethoxy; and $Ar^1$, $A^1$, $X$, $R^1$, $R^2$ and $R^3$ have any of the meanings defined hereinbefore;

(f) $Ar^2$ is 1,3-phenylene or 1,4-phenylene which may optionally bear one substituent selected from fluoro, chloro, hydroxy, amino, nitro, methoxy, methylamino, dimethylamino, trifluoromethyl and acetamido; and $Ar^1$, $A^1$, $X$, $R^1$, $R^2$, and $R^3$ have any of the meanings defined hereinbefore;

(g) $Ar^2$ is 2,4-, 2,5-, 3,5- or 2,6-pyridylene or 4,6-pyrimidylene; and $Ar^1$, $A^1$, $R^1$, $R^2$ and $R^3$ have any of the meanings defined hereinbefore; or (h) $Ar^2$ is 3,5-pyridylene; and $Ar^1$, $A^1$, $R^1$, $R^2$ and $R^3$ have any of the meanings defined hereinbefore;

(i) $R^1$ and $R^2$ together form a group of the formula $-A^2-X-A^3-$ which, together with the oxygen atom to which $A^2$ is attached and with the carbon atom to which $A^3$ is attached, defines a ring having 5 to 7 ring atoms, wherein $A^2$ and $A^3$, which may be the same or different, each is methylene, ethylene, ethylidene or isopropylidene and X is oxy, and $R^3$ is methyl or ethyl; and $Ar^1$, $A^1$ and $Ar^2$ have any of the meanings defined hereinbefore;

(j) $R^1$ and $R^2$ together form a group of the formula $-A^2-X-A^3-$ which, together with the oxygen atom to which $A^2$ is attached and with the carbon atom to which $A^3$ is attached, defines a ring having 5 or 6 ring atoms, wherein $A^2$ is methylene, ethylidene, propylidene, isopropylidene, butylidene, isobutylidene, isopentylidene, sec-butylidene, pentan-2-ylidene, pentan-3-ylidene, hexan-2-ylidene or cyclopentylidene; $A^3$ is methylene, ethylene or ethylidene and X is oxy or thio, and which ring may bear one substituent selected from hydroxy, methoxy, hydroxymethyl, 2-hydroxyethyl, methoxymethyl and 2-methoxyethyl; and $Ar^1$, $A^1$, $Ar^2$ and $R^3$ have any of the meanings defined hereinbefore; or (k) $R^3$ is methyl, ethyl, propyl, allyl, methoxymethyl, 2-methoxyethyl or 2-acetylethyl; and $Ar^1$, $A^1$, $Ar^2$, $R^1$ and $R^2$ have any of the meanings defined hereinbefore; or a pharmaceutically-acceptable salt thereof.

A preferred compound of the invention comprises a cyclic ether derivative of the formula I wherein $Ar^1$ is phenyl, naphth-1-yl or naphth-2-yl which may optionally bear one or two substituents selected from fluoro, chloro, cyano, methyl, methoxy, difluoromethyl and trifluoromethyl;

$A^1$ is methylene, 1-propenylene or 1-propynylene;

$Ar^2$ is 1,3-phenylene or 1,4-phenylene which may optionally bear one substituent selected from hydroxy, amino, nitro, methoxy, methylamino, cyanomethoxy and trifluoromethyl; or $Ar^2$ is 3,5-pyridylene;

$R^1$ and $R^2$ together form a group of the formula $-A^2-X-A^3-$ which, together with the oxygen atom to which $A^2$ is attached and with the carbon atom to which $A^3$ is attached, defines a ring having 5 ring atoms, wherein $A^2$ is methylene, ethylidene, isopropylidene or ethylene, $A^3$ is methylene and X is oxy, and $R^3$ is methyl or ethyl; or a pharmaceutically-acceptable salt thereof.

A preferred compound of the invention comprises a cyclic ether derivative of the formula I wherein $Ar^1$ is phenyl or naphth-2-yl which may optionally bear one or two substituents selected from fluoro, chloro, bromo, methyl, ethyl, propyl, tert-butyl and trifluoromethyl;

$A^1$ is methylene or 1-propynylene;

$Ar^2$ is 1,3-phenylene or 1,4-phenylene which may optionally bear one substituent selected from fluoro, amino, methoxy and trifluoromethyl;

$R^1$ and $R^2$ together form a group of the formula $-A^2-X-A^3-$ which, together with the oxygen atom to which $A^2$ is attached and with the carbon atom to which $A^3$ is attached, defines a ring having 5 ring atoms, wherein $A^2$ is methylene, ethylidene, propylidene, isopropylidene, butylidene, isobutylidene, sec-butylidene, pentan-2-ylidene, pentan-3-ylidene or cyclopenlylidene, $A^3$ is methylene or ethylidene and X is oxy, and which ring may bear one substituent selected from hydroxymethyl, methoxymethyl and 2-methoxyethyl; and $R^3$ is methyl, ethyl, allyl or 2-acetylethyl;

or a pharmaceutically-acceptable salt thereof.

A further preferred compound of the invention comprises a cyclic ether derivative of the formula I wherein $Ar^1$ is phenyl or naphth-2-yl-which may optionally bear one substituent selected from fluoro, methyl and trifluoromethyl;

$A^1$ is methylene or 1-propynylene;

$Ar^2$ is 1,3-phenylene or 1,4-phenylene which may optionally bear one substituent selected from fluoro, methoxy and trifluoromethyl;

$R^1$ and $R^2$ together form a group of the formula $-A^2-X-A^3-$ which, together with the oxygen atom to which $A^2$ is attached and with the carbon atom to which $A^3$ is attached, defines a ring having 5 ring atoms, wherein $A^2$ is propylidene, isopropylidene, isobutylidene, sec-butylidene and pentan-2-ylidene, $A^3$ is methylene or ethylidene and X is oxy, and $R^3$ is methyl or ethyl;

or a pharmaceutically-acceptable salt thereof.

A further preferred compound of the invention comprises a cyclic ether derivative of the formula I wherein $Ar^1$ is naphth-2-yl or 7-fluoronaphth-2-yl;

$A^1$ is methylene;

$Ar^2$ is 1,3-phenylene or 5-fluoro-1,3-phenylene;

$R^1$ and $R^2$ together form a group of the formula $-A^2-X-A^3-$ which, together with the oxygen atom to which $A^2$ is attached and with the carbon atom to which $A^3$ is attached, defines a ring having 5 ring atoms, wherein $A^2$ is isopropylidene, sec-butylidene or pentan-2-ylidene, $A^3$ is methylene or ethylidene and X is oxy, and $R^3$ is methyl or ethyl;

or a pharmaceutically-acceptable salt thereof.

A further preferred compound of the invention comprises a cyclic ether derivative of the formula I wherein $Ar^1$ is naphth-2-yl; $A^1$ is methylene;

$Ar^2$ is 1,3-phenylene;

$R^1$ and $R^2$ together form a group of the formula $-A^2-X-A^3-$ which, together with the oxygen atom to which $A^2$ is attached and with the carbon atom to which $A^3$ is attached, defines a ring having 5 ring atoms, wherein $A^2$ is isopropylidene, $A^3$ is methylene and X is oxy, and $R^3$ is ethyl;

or a pharmaceutically-acceptable salt thereof.

Specific especially preferred compounds of the invention include, for example, the following cyclic ether derivatives of the formula I, or pharmaceutically-acceptable salts thereof:

4-ethyl-2,2-dimethyl-4-[3-(naphth-2-ylmethoxy)-phenyl]-1,3-dioxolane, 2,2,4-trimethyl-4-[3-(naphth-2-ylmethoxy)phenyl]-1,3-dioxolane, (4RS,5RS)-2,2,4,5-tetramethyl-4-5-fluoro-3-(naphth-2-ylmethoxy)phenyl]-1,3-dioxolane, 2,4-diethyl-2-methyl-4-[3-naphth-2-ylmethoxy)phenyl]-1,3-dioxolane, 4-ethyl-4-[5-fluoro-3-(7-fluoronaphth-2-ylmethoxy)-phenyl]-2,2-dimethyl-1,3-dioxolane, 4-ethyl-2-methyl-4-[3-naphth-2-ylmethoxy) phenyl]-2-propyl-1,3-dioxolane, 2,4-diethyl-4-[5-fluoro-3-(7-fluoronaphth-2-ylmethoxy)-phenyl-1,3-dioxolane and (+)-4-3-(7-fluoronaphth-2-ylmethoxy) phenyl-2,4-dimethyl-2-propyl-1,3-dioxolane.

A compound of the invention comprising a cyclic ether derivative of the formula I, or a pharmaceutically-acceptable salt thereof, may be prepared by any process known to be applicable to the preparation of structurally-related compounds. Such procedures are provided as a further feature of the invention and are illustrated by the following $Ar^2$, $R^1$, $R^2$ and $R^3$ have any of the meanings defined hereinbefore.

(a) The alkylation, in the presence of a suitable base, of a compound of the formula II wherein $Ar^2$, $R^3$, $A^2$, $A^3$ and X have the meanings defined hereinbefore, with a compound of the formula $Ar^1$—$A^1$—Z wherein $Ar^1$ and $A^1$ have the meanings defined hereinbefore and Z is a displaceable group; provided that, when there is an amino, imino, alkylamino, hydroxy or carboxy group in $Ar^1$, $Ar^2$, X or $R^3$, any amino, imino, alkylamino or carboxy group is protected by a conventional protecting group and any hydroxy group may be protected by a conventional protecting group or alternatively any hydroxy group need not be protected; whereafter any undesired protecting group in $Ar^1$, $Ar^2$, X or $R^3$ is removed by conventional means.

A suitable displaceable group Z is, for example, a halogeno or sulphonyloxy group, for example a chloro, bromo, iodo, methanesulphonyloxy or toluene-p-sulphonyloxy group.

A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near ambient temperature.

A suitable protecting group for an amino, imino or alkylamino group is, for example, an acyl group for example a (1–4C)alkanoyl group (especially acetyl), a (1–4C)alkoxycarbonyl group (especially methoxycarbonyl, ethoxycarbonyl or t-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1–4C)alkyl group (especially methyl or ethyl) or an arylmethyl group (especially benzyl). The deprotection conditions for the above protecting groups necessarily vary with the choice of protecting group. Thus, for example, an esterifying group such as an alkyl or arylmethyl group may be removed, for example, by hydrolysis with a suitable base such as an alkali metal hydroxide, for example lithium or sodium hydroxide. Alternatively an esterifying group such as an arylmethyl group may be removed, for example, by hydrogenation over a catalyst such as palladium-on-charcoal.

A suitable protecting group for a hydroxy group is, for example, an acyl group, for example a (1–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula III may be obtained by standard procedures of organic chemistry. The preparation of examples of such starting materials is described within the accompanying non-limiting Examples which are provided for the purposes of illustration only. Other necessary starting materials are obtainable by analogous procedures to those described or by modifications thereto which are within the ordinary skill of an organic chemist. The starting material of the formula II may be obtained, for example, by deprotecting a protected ether derivative of the formula III wherein $R^4$ is a protecting group and $Ar^2$, $A^2$, X, $A^3$ and $R^3$ have the meanings defined hereinbefore.

A suitable protecting group $R^4$ is, for example, an arylmethyl group (especially benzyl), a tri-(1–4C)alkylsilyl group (especially trimethylsilyl or t-butyldimethylsilyl), an aryldi-(1–4C)-alkylsilyl group (especially dimethylphenylsilyl), a (1–4C)alkyl group (especially methyl), a (1–4C)alkoxymethyl group (especially methoxymethyl) or a tetrahydropyranyl group (especially tetrahydropyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryl dialkylsilyl group such as a t-butyldimethylsilyl or a dimethylphenylsilyl group may be removed, for example, by treatment with a suitable acid such as hydrochloric, sulphuric, phosphoric or trifluoroacetic acid or with an alkali metal or ammonium fluoride such as sodium fluoride or, preferably, tetrabutylammonium fluoride. Alternatively an alkyl group may be removed, for example, by treatment with an alkali metal (1-4C)alkylsulphide such as sodium thioethoxide or, for example, by treatment with an alkali metal diarylphosphide such as lithium diphenylphosphide. Alternatively a (1-4C)alkoxymethyl group or tetrahydropyranyl group may be removed, for example, by treatment with a suitable acid such as hydrochloric or trifluoroacetic acid.

The protecting group $R^4$ may be, for example, a tri-(1-4C)-alkylsilyl group which can be removed while the protecting group for any amino, imino, alkylamino, carboxy or hydroxy group in $Ar^2$, $R^3$ or the ring is retained.

The protected starting material of the formula III may be obtained by standard procedures of organic chemistry. Thus, for example, an alcohol of the formula $R^4$—O—$Ar^2$—CH (OH)—$R^3$, wherein $R^4$ is a protecting group as defined hereinbefore, may be obtained by the reaction of an aldehyde of the formula $R^4$—O—$Ar^2$—CHO with an organometallic compound of the formula $R^3$—M or $R^3$—M—Z, wherein $R^3$ has the meaning defined hereinbefore, M is a metallic group, for example lithium, magnesium or zinc, and Z is a halogeno group, for example chloro, bromo or iodo, and provided that any amino, alkylamino, or hydroxy group in $Ar^2$ or $R^3$ is protected by a conventional protecting group. The reaction may be carried out in, for example, a suitable solvent or diluent such as an ether (for example tetrahydrofuran, t-butylmethylether or diethyl ether) at a temperature in the range, for example, $-100°$ to $50°$ C. (especially $-80°$ to $30°$ C.).

The secondary alcohol of the formula $R^4$—O—$Ar^2$—CH(OH)—$R^3$ may be oxidised to give a ketone of the formula $R^4$—O—$Ar^2$—CO—$R^3$. A particular suitable oxidising agent is, for example, any agent known in the art for the oxidation of a secondary alcohol to a ketone, for example, manganese dioxide, chromium trioxide pyridine complex, 2,3-dichloro-5,6-dicyano-1,4-benzoquinone (hereinafter DDQ), a mixture of dimethylsulphoxide, oxalyl chloride and triethylamine, a mixture of acetic anhydride and dimethylsulphoxide or a mixture of dimethylsulphoxide and a dialkylcarbodiimide, for example N,N'-dicyclohexylcarbodiimide or N-ethyl-N'-(3-dimethylaminopropyl)carbodiimide.

A tertiary alcohol of the formula IV, wherein $R^4$ has the meaning defined hereinbefore, may be obtained by the reaction of the ketone $R^4$—O—$Ar^2$—CO—$R^3$ with an organometallic compound of the formula $R^5$—X—$A^3$—M—Z, wherein M is a metallic group, for example magnesium, and Z is a halogeno group, for example chloro, bromo or iodo, and $R^5$ is a suitable protecting group as defined below, and provided that any amino, alkylamino or hydroxy group in $Ar^2$ or $R^3$ is protected by a conventional protecting group. The reaction may be carried out in a suitable solvent or diluent such as an ether (for example tetrahydrofuran, t-butyl- methyl ether or diethyl ether) at a temperature in the range, for example, $-30°$ to $100°$ C. (especially ambient temperature to $80°$ C.).

$R^5$, when it is a suitable protecting group for an amino or hydroxy group, has one of the meanings defined hereinbefore. A suitable protecting group for a mercapto group is, for example, an acyl group, for example a (1-4C)alkanoyl group (especially acetyl) or an aroyl group (especially benzoyl). An acyl group such as an alkanoyl or an aroyl group may be removed, for example, by hydrolysis with a suitable base such as an alkali metal hydroxide, for example lithium or sodium hydroxide.

It will be appreciated that the tertiary alcohol of the formula IV may be obtained from &he aldehyde of the formula $R^4$—O—$Ar^2$—CHO by reversing the order of introduction of the groups $R^3$ and $R^5$—X—$A^3$—. Thus the aldehyde of the formula $R^4$—O—$Ar^2$—CHO may be treated initially with the organometallic compound of the formula $R^5$—X—$A^3$—M—Z, the product so obtained may be oxidise using a suitable oxidising agent as described above and the resultant ketone may be treated with the organometallic compound $R^3$—M or $R^3$—M—Z to give the compound of the formula IV, and provided that any amino, alkylamino or hydroxy group in $Ar^2$ or $R^3$ is protected by a conventional protecting group.

The cyclic ether derivative of the formula III, wherein $R^4$ has the meaning defined hereinbefore, may be obtained from the tertiary alcohol of the formula IV by the removal of the protecting group $R^5$, while the protecting group for any amino, alkylamino, carboxy or hydroxy group in $Ar^2$ or $R^3$ is retained, and cyclisation in the presence of a suitable base of the compound of the formula V so formed by reaction with a compound of the formula Z—$A^2$—Z, wherein Z is a suitable displaceable group as defined hereinbefore, or the cyclisation in the presence of a suitable acid, for example hydrochloric, sulphuric, phosphoric, trifluoroacetic or p-toluenesulphonic acid, or a Lewis acid such as a boron trihalide, for example boron trifluoride, of the compound of the formula V so formed by reaction with a (1-3C)aldehyde, for example formaldehyde or acetaldehyde, or with a (1-3C)ketone, for example acetone, or with corresponding hemiacetal or acetal derivatives thereof.

Alternatively the tertiary alcohol starting material of the formula IV may be obtained by the reaction of a compound of the formula $R^4$—O—$Ar^2$—Z wherein $R^4$ and $Ar^2$ have the meanings defined hereinbefore and Z is a halogeno group as defined hereinbefore and provided that any amino, alkylamino or hydroxy group in $Ar^2$ is protected with a conventional protecting group, with either an organometallic compound of the formula $R^6$—M, wherein $R^6$ is a (1-6C)alkyl group such as butyl and H is a metallic group, for example lithium, to give an organometallic compound of the formula $R^4$—O—$Ar^2$—M, or with a metal such as magnesium to given an organometallic compound of the formula $R^4$—O—$Ar^2$—M—Z; whereafter either of these organometallic compounds may be reacted with a ketone of the formula $R^3$—CO—$A^3$—X—$R^5$, wherein $R^3$, $A^3$, X and $R^5$ have the meanings defined hereinbefore, and provided that any hydroxy group in $R^3$ is protected by a conventional protecting group.

(b) The cyclisation, in the presence of a suitable base as defined hereinbefore, of a compound of the formula VI by reaction with a compound of the formula Z—$A^2$—Z, wherein $A^2$ and Z have the meanings defined hereinbefore, provided that, when there is an amino, alkylamino, hydroxy or carboxy group in $Ar^1$, $Ar^2$ or $R^3$, any amino, alkylamino, hydroxy or carboxy group is protected by a conventional protecting group; whereafter any undesired protecting group in $Ar^1$, $Ar^2$ or $R^3$, is removed by conventional means.

The tertiary alcohol starting material of the formula VI may be obtained, for example, by the reaction of an aldehyde of the formula $Ar^1-A^1-O-Ar-CHO$ with an organometallic compound of the formula $R^3-M$ or $R^3-M-Z$, having the meaning defined hereinbefore and using the conditions defined hereinbefore, to give a secondary alcohol of the formula $Ar^1-A^1-O-Ar^2-CH(OH)-R^3$ and provided that any amino, alkylamino, carboxy or hydroxy group in $Ar^1$, $Ar^2$ or $R^3$ is protected by a conventional protecting group. The product so obtained may be oxidised using a suitable oxidising agent, as defined hereinbefore, to give a ketone of the formula $Ar^1-A^1-O-Ar^2-CO-R^3$, which in turn may be treated with an organometallic compound of the formula $R^5-X-A^3-M-Z$, having the meaning defined hereinbefore and using the conditions defined hereinbefore, to give he tertiary alcohol of the formula VII, whereafter the protecting group $R^5$ may be removed using the conditions defined hereinbefore to give the required tertiary alcohol starting material of the formula VI.

It will be appreciated that the tertiary alcohol of the formula VII may be obtained from the aldehyde of the formula $Ar^1-A^1-O-Ar^2-CHO$ by reversing the order of the introduction of the groups $R^5-X-A^3-$, i.e. by reaction of the aldehyde of the formula $Ar^1-A^1-O-Ar^2-CHO$ with the organometallic compound of the formula $R^5-X-A^3-M-Z$, oxidation of the secondary alcohol to a ketone of the formula $Ar^1-A^1-O-Ar^2-CO-A^3-X-R^5$ and reaction of said ketone with the organometallic compound of the formula $R^3-M$ or $R^3-M-Z$, and provided that any amino, alkylamino, carboxy or hydroxy group in $Ar^1$, $R^2$ or $R^3$ is protected by a conventional protecting group.

Alternatively the ketone intermediate of the formula $Ar^1-A^1-O-Ar^2-CHO$ may be obtained, for example, by the alkylation, in the presence of a suitable base as defined hereinbefore, of a ketone of the formula $HO-Ar^2-CO-A^3-X-R^5$ with a compound of the formula $Ar^1-A^1-Z$, wherein Z is a displaceable group as defined hereinbefore, and provided that any amino, alkylamino, carboxy or hydroxy group in $Ar^1$ or $Ar^2$ is protected by a conventional protecting group.

The aldehyde starting material of the formula $Ar^1-A-O-Ar^2-CHO$ may be obtained, for example, by the alkylation, in the presence of a suitable base as defined hereinbefore, of an aldehyde of the formula $H-O-Ar^2-CHO$ with a compound of the formula $Ar^1-A^1-Z$, wherein Z is a displaceable group, as defined hereinbefore, and provided that any amino, alkylamino, carboxy or hydroxy group in $Ar^1$ or $Ar^2$ is protected by a conventional protecting group.

Alternatively he tertiary alcohol of the formula VII may be obtained, for example, by the reaction of an ester of the formula $Ar^1-A^1-O-Ar^2-CO_2R^6$, wherein $R^6$ is a (1-4C)alkyl group such as methyl or ethyl, with an organometallic compound of the formula $R^3-M$ or $R^3-M-Z$, having the meaning defined hereinbefore and using the conditions defined hereinbefore for the corresponding reaction of the aldehyde of the formula $R^4-O-Ar^2-CHO$, and provided that any amino, alkylamino, carboxy or hydroxy group in $Ar^1$, $Ar^2$ or $R^3$ is protected by a conventional protecting group, to give a ketone of the formula $Ar^1-A^1-O-Ar^2-CO-R^3$. The product so obtained may be treated with an organometallic compound of the formula $R^5-X-A^3-M-Z$, having the meaning defined hereinbefore and using the conditions defined hereinbefore, to give the tertiary alcohol of the formula VII.

It will be appreciated that the tertiary alcohol of the formula VII may be obtained from the ester of the formula $Ar^1-A^1-O-Ar^2-R^6$ by reversing the order of the introduction of the groups $R^3$ and $R^5-X-A^3-$, i.e. by reaction of the ester of the formula $Ar^1-A^1-O-Ar^2-CO_2R^6$ with the organometallic compound of the formula $R^5-X-A^3-M-$ to give a ketone of the formula $Ar^1-A^1-O-Ar^2-CO-A^3-X-R^5$ and reaction of said ketone with the organometallic compound of the formula $R^3-M$ or $R^3-M-Z$ and provided that any amino, alkylamino, carboxy or hydroxy group in $Ar^1$, $Ar^2$ or $R^3$ is protected by a conventional protecting group.

The ester starting material of the formula $Ar^1-A^1-O-Ar^2-CO_2R^6$ may be obtained, for example, by the alkylation, in the presence of a suitable base as defined hereinbefore, of an ester of the formula $H-O-Ar^2-CO_2R^6$, wherein $R^6$ has the meaning defined hereinbefore, with a compound of the formula $Ar^1-A^1-Z$, wherein Z is a displaceable group as defined hereinbefore, and provided that any amino, alkylamino, carboxy or hydroxy group in $Ar^1$ or $Ar^2$ is protected by a conventional protecting group.

Alternatively the ketone of the formula $Ar^1-A^1-O-Ar^2-CO-R^3$ may be obtained by the reaction of a nitrile of the formula $Ar^1-A^1-O-Ar^2-CN$ with an organometallic compound of the formula $R^3-M$ or $R^3-M-Z$ using the conditions defined hereinbefore for the corresponding reaction of the aldehyde of the formula $R^3-O-Ar^2-CHO$.

Alternatively the tertiary alcohol of the formula VII may be obtained, for example, by the alkylation, in the presence of a suitable base, of a compound of the formula $HO-Ar^2-Z$, wherein $Ar^2$ has the meaning defined hereinbefore and Z is a halogeno group as defined hereinbefore, with a compound of the formula $Ar^1-A^1-Z$, wherein $Ar^1$, $A^1$ and Z have the meanings defined hereinbefore, and provided that any amino, alkylamino, carboxy or hydroxy group in $Ar^1$ or $Ar^2$ is protected by a conventional protecting group, to give a compound of the formula $Ar^1-A^1-O-Ar^2-Z$. The product so obtained may be treated either with an organometallic compound of the formula $R^7-M$, wherein $R^7$ is a (1-6C)alkyl group such as butyl and M is a metallic group, for example lithium, to give an organometallic compound of the formula $Ar^1-A^1-O-Ar^2-M$, or with a metal such as magnesium to give an organometallic compound of the formula $Ar^1-A^1-O-Ar^2-M-Z$. Either of these organometallic compounds may be reacted with a ketone of the formula $R^3-CO-A^3-X-R^5$, provided that any hydroxy group in $R^3$ is protected by a conventional protecting group, to give the tertiary alcohol of the formula VII.

(c) The cyclisation, in the presence of a suitable acid as defined hereinbefore, of a compound of the formula VI by reaction with a (1-3C)aldehyde or with a (1-3C)ketone, or with corresponding hemiacetal or acetal derivatives thereof, provided that, when there is an amino, alkylamino, hydroxy or carboxy group in $Ar^1$, $Ar^2$ or $R^3$, any amino, alkylamino, hydroxy or carboxy group is protected by a conventional protecting group; whereafter any undesired protecting group in $Ar^1$, $Ar^2$ or $R^3$ is removed by conventional means.

The tertiary alcohol starting material of the formula VI may be obtained as defined hereinbefore.

(d) For the production of those compounds of the formula I wherein $A^1$ is a (3–6C)alkynylene group, the coupling, in the presence of a suitable organometallic catalyst, of a compound of the formula $Ar^1$—Z wherein $Ar^1$ has the meaning defined hereinbefore and Z is a halogeno group such as iodo, with an ethynyl compound of the formula VIII, wherein A is (1–4C)alkylene and $Ar^2$, $A^2$, X, $A^3$ and $R^3$ have the meanings defined hereinbefore.

A suitable organometallic catalyst is, for example, any agent known in the art for such a coupling reaction. Thus, for example, a suitable reagent is formed when, for example, bis(triphenylphosphine)palladium chloride or tetrakis(triphenylphosphine)palladium and a copper halide, for example curpous iodide, are mixed. The coupling is generally carried out in suitable inert solvent or diluent, for example acetonitrile, 1,2-dimethoxyethane, toluene or tetrahydroiuran, at a temperature in the range, for example, 10° to 80° C., conveniently at or near 50° C., and in the presence of a suitable base such as, for example, a tri-(1–4C)alkylamine such as triethylamine, or a cyclic amine such as piperidine.

The ethynyl compound of the formula VIII, used as a starting material, may be obtained, for example, by the alkylation, in the presence of a suitable base, of a compound of the formula II, wherein $Ar^2$, $A^2$, X, $A^3$ and $R^3$ have the meanings defined hereinbefore, with an alkylating agent of the formula H—C≡C—A—Z, wherein A has the meaning defined hereinbefore and Z is a halogeno group, and provided that any amino, imino, alkylamino, carboxy or hydroxy group in $Ar^2$, X or $R^3$ is protected by a conventional protecting group.

(e) For the production of those compounds of the formula I wherein $Ar^1$ or $Ar^2$ bears an alkylsulphinyl or alkylsulphonyl substituent or wherein $R^1$ and $R^2$ together form a group of the formula —$A^2$—X—$A^3$— and X is a sulphinyl or sulphonyl group, the oxidation of a compound of the formula I wherein $Ar^1$ or $Ar^2$ bears an alkylthio substituent or wherein X is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or t-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(f) For the production of those compounds of the formula I wherein $Ar^2$ bears an alkanoylamino substituent, the acylation of a compound of the formula I wherein $Ar^2$ bears an amino substituent.

A suitable acylating agent is, for example, any agent known in the art for the acylation of amino to acylamino, for example an acyl halide, for example a (2–6C)alkanoyl chloride or bromide, in the presence of a suitable base, an alkanoic acid anhydride, for example a (2–6C)alkanoic acid anhydride, or an alkanoic acid mixed anhydride, for example the mixed anhydride formed by the reaction of an alkanoic acid and a (1–4C)alkoxycarbonyl halide, for example a (1–4C)alkoxycarbonyl chloride, in the presence of a suitable base. In general the reaction is carried out in a suitable solvent or diluent such as methylene chloride, acetone, tetrahydrofuran or t-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(g) For the production of those compounds of the formula I wherein $Ar^1$ bears an alkenyl substituent, $A^1$ is alkenylene or wherein $R^1$ and $R^2$ together from a group of the formula —$A^2$—X—$A^3$— and $R^3$ is alkenyl, the reduction of the corresponding compound wherein $Ar^1$ bears an alkynyl substituent, $A^1$ is alkynylene or $R^3$ is alkynyl. In general conditions which are standard in the art for the reduction of an alkynyl or alkynylene group are used. Thus, for example, the reduction may be carried out by the hydrogenation of a solution of the alkynyl or alkynylene compound in an inert solvent or diluent in the presence of a suitable metal catalyst. A suitable inert solvent is, for example, an alcohol, for example methanol or ethanol, or an ether, for example tetrahydrofuran or t-butyl methyl ether. A suitable metal catalyst is, for example, palladium or platinum on an inert support, for example charcoal or barium sulphate.

Preferably a palladium-on-barium sulphate catalyst is used to substantially prevent over-reduction of the alkynyl or alkynylene group to an alkyl or alkylene group respectively. The reaction is generally carried out at a temperature at or near ambient temperature, that is in the range 15° to 35° C.

Alternatively the reduction may be carried out by treating a solution of the alkynyl or alkynylene compound in an inert solvent or diluent with a suitable mixture such as a 1:1 mixture of an organometallic hydride, for example a di-(1–6C)alkylaluminium hydride such as diisobutylaluminium hydride, and an alkyl metal, for example a (1–6C)alkyl lithium such as methyl lithium. A suitable inert solvent or diluent is, for example, tetrahydrofuran, diethyl ether or t-butyl methyl ether and, in general, the reaction is carried out at a temperature, for example, in the range −25° C. to ambient temperature (especially −10° to 10° C.).

(h) For the production of those compounds of the formula 1 wherein $Ar^2$ bears an alkoxy or substituted alkoxy substituent, the alkylation of a compound of the formula I wherein $Ar^2$ bears a hydroxy substituent.

A suitable alkylating agent is, for example any agent known in the art for the alkylation of hydroxy to alkoxy or substituted alkoxy, for example an alkyl or substituted alkyl halide, for example a (1–6C)alkyl chloride, bromide or iodide or a substituted (1–4C)alkyl chloride, bromide or iodide, in the presence of a suitable base. A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide dimethylsulphoxide, acetone, 1,2-dimethoxyethane or tetrahydrofuran, and at a temperature in the range, for example, 10° to 150° C., conveniently at or near ambient temperature.

(i) For the production of those compounds of the formula I wherein $Ar^2$ bears an amino substituent, the reduction of a compound of the formula I wherein $Ar^2$ bears a nitro substituent.

A suitable reducing agent is, for example, any agent known in the art for the reduction of a nitro group to an amino group. Thus, for example, the reduction may be carried out by the hydrogenation of a solution of the nitro compound in an inert solvent or diluent in the presence of a suitable metal catalyst, for example finely divided platinum metal (obtained by the reduction of platinum oxide in situ). A suitable inert solvent or diluent is, for example, an alcohol, for example methanol, ethanol or isopropanol, or an ether, for example tetrahydrofuran.

A further suitable reducing agent is, for example, an activated metal such as activated iron (produced by washing iron powder with a dilute solution of an acid such as hydrochloric acid). Thus, for example, the reduction may be carried out by heating a mixture f the nitro compound and the activated metal in a suitable solvent or diluent such as a mixture of water and an alcohol, for example, methanol or ethanol, to a temperature in the range, for example, 50° to 150° C. conveniently at or near 70° C.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae II, III, IV, V, VI and VII and these are provided as a further feature of the invention.

As stated previously, the cyclic ether derivatives of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (J. Biol. Chem., 1986, 261(25), 11512-11519). This test provides a measure of the intrinsic inhibitory properties against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, Brit. J. Pharmacol. 1985, 84, 34P) which involves the use of a protein-$LTB_4$ conjugate produced using the procedure of Young et alia (Prostaglandins, 1983, 26(4),605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2 (T \times B_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $T \times B_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, Biochem. Pharmacol., 1983, 32, 2319-2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (Brit. J. Pharmacol., 1986, 89, 431-438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a $\beta$-adrenergic blocking agent (propranolol) and a cyclooxygenase inhibitor (indomethacin), using the procedure of W. H. Anderson et alia (British J Pharmacology, 1983, 78(1), 67-574). This test provides a further in vivo test for detecting 5-LO inhibitors.

Although the pharmacological properties of the compounds of the formula I vary with structural changes as expected, in general compounds of the formula I possess 5-LO inhibitory effects at the following concentrations or doses in one or more of the above tests a)-f):

Test a): $IC_{50}$ in the range, for example, 0.01-30 $\mu M$;

Test b): $IC_{50}$ ($LTB_4$) in the range, for example, 0.01-40 $\mu M$; $IC_{50}$ ($TxB_2$) in the range, for example, 40-200 $\mu M$;

Test c): oral $ED_{50}$ ($LTB_4$) in the range, for example, 1-200 mg/kg;

Test d): $IC_{50}$ ($LTC_4$) in the range, for example, 0.001-1 $\mu M$; $IC_{50}$ ($PGE_2$) in the range, for example, 20-1000 $\mu M$;

Test e): inhibition of inflammation in the range, for example, 0.3-100 $\mu g$ intradermally;

Test f): $ED_{50}$ in the range, for example, 0.5-10 mg/kg i.v.

No overt toxicity or other untoward effects are present in tests c), e) and/or f) when compounds of the formula I are administered at several multiples of their minimum inhibitory dose or concentration.

Thus, by way of example, the compound 4-ethyl-2,2-dimethyl-4-[3-(naphth-2-ylmethoxy)phenyl]-1,3-dioxolane has an $IC_{50}$ of 0.1 $\mu M$ against $LTS_4$ and of >40 $\mu M$ against $TxB_2$ in test b). In general those compounds of the formula I which are particularly preferred have an $IC_{50}$ of <1 $\mu M$ against $LTB_4$ and of >40 $\mu M$ against $TxB_2$ in test b), and an oral $ED_{50}$ of <100 mg/kg against $LTB_4$ in test c).

These compounds are examples of cyclic ether derivatives of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a cyclic ether derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of active ingredient (that is a cyclic ether derivative of the formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a cyclic ether derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of an cyclic ether derivative of the formula I will naturally vary according to the nature and severity of the conditions, the age and sex of the animal or patient and the route of administration, according to well known principles of medicine. As mentioned above, cyclic ether derivatives of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a cyclic ether derivative of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The compounds of the formula I may also be used in combination with leukotriene antagonists such as those disclosed in European Patent Specifications Nos. 179619, 199543, 220066, 227241, 242167, 290145, 337765, 337766 and 337767, which are incorporated herein by way of reference.

The invention will now be illustrated in the following non-limiting Examples in which, unless otherwise stated:

(i) evaporations were carried out by rotary evaporations in vacuo and work-up procedures were carried out after removal of residual solids by filtration;

(ii) operations were carried out at room temperature, that is in the range 18°-20° and under an atmosphere of an inert gas such as argon;

(iii) column chromatography (by the flash procedure) and medium pressure liquid chromatography (MPLC) were performed on Merck Kieselgel silica (Art. 9385) obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus; melting points for the end-products of the formula I were determined after recrystallisation from a conventional organic solvent such as ethanol, methanol, acetone, ether or hexane, alone or in admixture, and (viii) the specific rotation, $[\alpha]'$, of plane polarised light was determined using the sodium D line (5890 Angstroms), at 20° C., and generally using sample concentrations of approximately 1 g/100 ml of solvent.

EXAMPLE 1

A mixture of 2-[3-(naphth-2-ylmethoxy)phenyl]butane-1,2-diol (2 g), acetone (50 ml) and concentrated sulphuric acid (1 drop) was stirred at ambient temperature for 2 hours. The mixture was neutralised by adding 2N aqueous sodium hydroxide solution and evaporated. The residue was purified by column chromatography using a 4:1 v/v mixture of methylene chloride and petroleum ether (b.p. 60°-80° C.) as eluent. There was thus obtained 4-ethyl-2,2-dimethyl-4-[3-(naphth-2-ylmethoxy)phenyl]-1,3-dioxolane (1.85 g, 85%), m.p. 83°-84° C.

The butane-1,2-diol starting material was obtained as follows:

Alkylation of a solution of 3-cyanophenol in dimethylformamide with 2-bromomethylnaphthalene in the presence of potassium carbonate gave 3-(naphth-2-ylmethoxy)benzonitrile, m.p. 91°-93° C. This material was treated with ethylmagnesium bromide using the procedure described in *Organic Synthesis, Collect. Vol. III*, p.26, to give 3-(naphth-2-ylmethoxy)propiophenone, m.p. 56°-57° C.

A solution of this product (6 g) in tetrahydrofuran (12 ml) was added dropwise to a solution of isopropoxydimethylsilymethylmagnesium chloride [prepared, as described in *J. Org. Chem.*, 1983, 48, 2120, from chloromethylisopropoxydimethylsilane (8.2 ml) and magnesium powder (1.09 g) in tetrahydrofuran (2 ml)]. The mixture was stirred at ambient temperature for 1 hour, washed with a saturated aqueous solution of ammonium chloride and then with a saturated aqueous solution of sodium chloride. The organic layer was separated, dried (MgSO4) and evaporated to give 1-isopropoxydimethylsily-2-[3-(naphth-2-ylmethoxy)phenyl]butan-2-ol, as a yellow oil.

A mixture of the product so obtained, sodium bicarbonate (1.73 g), hydrogen peroxide (18 ml, 30% w/v in water), methanol (60 ml) and tetrahydrofuran (60 ml) was heated to reflux for 15 hours. The mixture was evaporated to remove the organic solvents and the residue was extracted with diethyl ether. The organic layer was separated, washed with a saturated aqueous solution of sodium chloride, dried (MgSO4) and evaporated. The residue was purified by column chromatography using initially methylene chloride and then increasingly polar mixtures of methylene chloride and acetone, up to a 9:1 v/v mixture, as eluent. There was thus obtained 2-[3-(naphth-2-ylmethoxy)phenyl]butane-1,2-diol (5.4 g, 81%), m.p. 100°-101° C.

EXAMPLE 2

The procedure described in Example 1 was repeated using the appropriate diol and the appropriate aldehyde or ketone in place of acetone. There were thus obtained the compounds described in the following table:

TABLE I

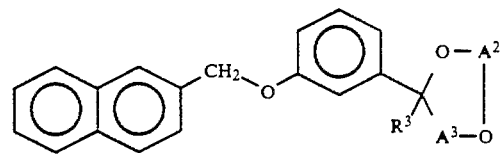

| Ex. 2 Compd. No. | $R^3$ | $A^2$ | $A^3$ | m.p. (°C.) | Yield (%) |
|---|---|---|---|---|---|
| 1*a* | Me | C(Me)2 | CH2 | 74–75 | 61 |
| 2*b,* | Et | CH2 | CH2 | 72–73 | 8 |
| 3*c* | Et | CH(Et) | CH2 | oil | 81 |
| 4*d* | Et | CH(Me) | CH2 | 94–97 | 84 |
| 5*e* | Et | C(Et)2 | CH2 | 97 | 96 |
| 6*f* | Et | C (CH2)4 | CH2 | oil | 83 |
| 7*g,* | Et | C(Me)2 | (CH2)2 | 92–93 | 54 |
| 8*h,+* | Et | C(Me)(Et) | CH2 | 84 | 28 |
| 9*h,+* | Et | C(Me)(Et) | CH2 | 71–72 | 29 |
| 10*i,+* | Et | C(Me)(Pr*n*) | CH2 | oil | 20 |
| 11*j,+* | Et | C(Me)(Bu*n*) | CH2 | oil | 43 |
| 12*j,+* | Et | C(Me)(Bu*n*) | CH2 | oil | 32 |
| 13*k,+* | Me | C(Me)(Pr*n*) | CH2 | oil | 38 |
| 14*l,+* | Me | C(Me)(Pr*n*) | CH2 | oil | 35 |

NOTES
*In these cases p-toluenesulphonic acid was used in place of concentrated sulphuric acid to catalyse the cyclisation.
+In these cases boron trifluoride etherate (2 equivalents) was used in place of concentrated sulphuric acid to catalyse the cyclisation, and ether was used as the reaction solvent.

a. The 2-3-(naphth-2-ylmethoxy)phenylpropane-1,2-diol, used as a starting material, was obtained as follows:

Using the procedure described in the Portion of Example 1 which is concerned with the preparation of starting materials, 3-hydroxyacetophenone was reacted with 2-bromomethylnaphthalene to give 3-(naphth-2-ylmethoxy)acetophenone, m.p. 88°–89° C. Following the procedure described in that portion of Example 1, the product so obtained was reacted with isopropoxydimethylsilylmethylmagnesium chloride and the resultant product was oxidised with hydrogen peroxide. There was thus obtained the required starting material in 40% overall yield, m.p. 119°–120° C.

b. Paraformaldehyde was used in place of the acetone utilised in Example 1. Benzene (50 ml) was used as a reaction solvent.

c. Methylene chloride was used as the reaction solvent. The product was obtained as a 3:1 mixture of diastereoisomers and displayed the following characteristic NMR signals (CDCl$_3$, delta values) 0.8–0.95(2 t's, 6H), 1.6–2.05(m, 4H), 3.97 and 4.05(2 q's, 2H), 4.9 and 5.1(2 t's, 1H), 5.25(s, 2H), 6.8–8.0(m, 11H).

d. The product was obtained as a 50:50 mixture of diastereoisomers which were separated by column chromatography eluting with a 4:1 v/v mixture of methylene chloride and petroleum ether (b.p. 40°–60° C.). There were thus obtained a less-polar isomer, m.p. 105°–108° C., and a more polar isomer, m.p. 63°–65° C.

e. Methylene chloride was used as the reaction solvent.

f. Cyclopentanone was used as the appropriate ketone and methylene chloride was used as the reaction solvent. The product displayed the following characteristic NMR signals (CDCl$_3$, delta values) 0.72(t, 3H), 1.5–2.0(m, 10H), 4.0(q, 2H), 5.23(s, 2H), 6.8–7.9(m, 11H).

g. Dimethylformamide was used as the reaction solvent and 2-methoxypropene was used in place of acetone.

The 3-[3-(naphth-2-ylmethoxy)phenylpentane-1,3-diol, used as a starting material was obtained as follows:

A mixture of 3-(naphth-2-ylmethoxy)propiophenone (8.7 g), ethyl bromoacetate (5 ml), powdered zinc (2 g), a crystal of iodine and tetrahydrofuran (30 ml) was heated to 60° C. for 30 minutes. The mixture was poured into water (50 ml), neutralised by adding 2N aqueous hydrochloric acid, and extracted with diethyl ether. The organic extract was dried (MgSO$_4$) and evaporated. The residue was purified by column chromatography using methylene chloride as eluent. There was thus obtained ethyl 3-hydroxy-3-[3-(naphth-2-ylmethoxy)phenyl]pentanoate (11.4 g, 100%), m.p. 61°–62° C.

A mixture of the product so obtained, lithium aluminium hydride and diethyl ether was stirred at ambient temperature for 1 hour. Any excess of reducing agent was destroyed by the careful addition of ethyl acetate and then water. The organic phase was separated dried (MgSO$_4$) and evaporated. There was thus obtained the required starting material m p. 77°–78° C.

h. The product was obtained as a mixture of diastereoisomers which were separated by column chromatography using toluene as eluent. There were thus obtained a less polar isomer (Compound No. 8) and a more polar isomer (Compound No. 9).

i. A mixture of diasterecisomers was obtained and after column chromatography the more polar isomer (Compound No. 10) was obtained in pure form. This product gave the following characteristic NMR signals (CDCl$_3$, delta values) 0.6–1.0(m, 6H), 1.2–1.7(m, 7H), 1.7–2.0(m, 2H), 4.1(d of d's, 2H), 5.25(s, 2H), 6.75–8.0(m, 11H).

j. The product was obtained as a mixture of diastereoisomers which were separated by column chromatography using toluene as eluent. There were thus obtained a less polar isomer (Compound No. 11), NMR Spectrum (CDCl$_3$, delta values) 0.6–1.0(2 t's, 6H), 1.15(s, 3H), 1.15–2.0(m, 8H), 4.05(s, 2H), 5.2(s, 2H), 6.75–8.0(m, 11H); and a more polar isomer (Compound No. 12), NHR Spectrum (CDCl$_3$, delta values) 0.7–0.95(2 t's, 6H), 1.0–2.0(m, 11H), 4.05(m, 2H), 5.24(s, 2H), 6.75–8.0(m, 11H).

k. The diol starting material was (+)-2-[3-(naphth-2-ylmethoxy)phenyl]propane-1,2-diol, $[\alpha]^{20} = +2.5°$ (methanol, c=1.001 g/100 ml). The product was obtained as a mixture of diastereoisomers from which the more polar isomer was obtained in pure form by column chromatography. This product displayed the following characteristic NMR signals (CDCl$_3$, delta values) 0.87(t, 3H), 1.15–1.84(m, 10H), 4.05(s, 2H), 5.24(s, 2H), 6.75–8.0(m, 11H); and an optical rotation $[\alpha]^{20} = +1.1°$ (methanol, conc=1.065 g/100 ml).

The (+)-2-[3-(naphth-2-ylmethoxy)phenyl]propane-1,2-diol, used as a starting material, was obtained as follows:

(-)-Phenylethylamine (1.88 g) was added to a solution of 2-hydroxy-2-[3-(naphth-2-ylmethoxy)phenyl]propionic acid (5 g) in acetone (25 ml) and the solution was stored overnight at 0° C. The salt which had been deposited was filtered off, washed with cold acetone, and recrystallised twice from acetone. There was thus obtained the ammonium salt (2.15 g). This salt was partitioned between ethyl acetate and dilute aqueous hydrochloric acid. The organic phase was washed with water, dried (HgSO$_4$) and evaporated. There was thus obtained (+)-2-hydroxy-2-[3-(naphth-2-ylmethoxy)phenyl]propionic acid (1.54 g, 61%), m.p. 149°–151° C., $[\alpha]^{20} = +11.7°$ (methanol, c=0.962 g/100 ml).

A solution of diazomethane in diethyl ether was added dropwise to a suspension of the acid so obtained in methylene chloride (20 ml), which had been cooled to 0° C., until the reaction mixture retained a yellow colouration. The mixture was stirred at 0° C. for 30 minutes. The mixture was evaporated and the residue was triturated under a mixture of petroleum ether (b.p. 60°–80° C.) and diethyl ether to give the methyl ester (1.52 g, 97%), m.p. 100°–102° C., $[\alpha]^{20} = +2°$ (methanol c=1 015 g/100 ml).

A solution of the ester so obtained in tetrahydrofuran (15 ml) was added dropwise to a stirred suspension of lithium aluminium hydride (0.255 g) in tetrahydrofuran (10 ml) which had been cooled to 0° C. The mixture was stirred for 1 hour. Water was then carefully added dropwise. The mixture was filtered and the filtrate was evaporated. There was thus obtained the required starting material (1.22 g, 88%), m.p. 105°–107° C., $[\alpha]^{20} = +2.5°$ (methanol, c=1.001 g/100 ml).

l. The diol starting material was (−)-2-[3-(naphth-2-ylmethoxy)phenyl]propane-1,2-diol, $[\alpha]^{20} = -3.86°$ C. (methanol, c=1.037 g/100 ml). The product was obtained as a mixture of diastereoisomers from which the more polar isomer was obtained in pure form by column chromatography. This product displayed the following characteristic NMR signals (CDCl$_3$, delta values) 0.85(t, 3H), 1.15–1.18(m, 10H), 4.06(s, 2H), 5.24(s, 2H), 6.75–8.0(m, 11H); and an optical rotation $[\alpha]^{20} = -1.9°$ (methanol, c=1.308 g/100 ml).

The (−)-2-[3-(naphth-2-ylmethoxy)phenyl]propane-1,2-diol, used as a starting material, was obtained as follows:

The mother liquors from the salt formation step described in Note k. above were partitioned between ethyl acetate and dilute aqueous hydrochloric acid. The organic phase was washed with water, dried (MgSO$_4$) and evaporated. The propionic acid so obtained (3.02 g) was dissolved in acetone (90 ml) and (+)-phenylethylamine (1.14 g) was added. The solution was stored overnight at 0° C. The free acid was isolated using the procedure described in Note k. above to give (−)-2-hydroxy-2-[3-(naphth-2-ylmethoxy)phenyl]propionic acid (1.65 g, 66%), m p. 153°-154° C., [α]$^{20}$ = −10.6° (methanol, c = 1.04 g/100 ml).

The procedure of ester formation and reduction, as described in Note k., were used to produce the required starting material, in 96% yield, m.p. 104°-106° C., [α]$^{20}$ = −3.86° (methanol, c = 1.037 g/100 ml).

EXAMPLE 3

A mixture of 2-[3-(naphth-2-ylmethoxy)phenyl]butane-1,2-diol (1.29 g), 2-methoxyacetaldehyde dimethyl acetal (1 ml), p-toluenesulphonic acid 20 mg) and toluene (20 ml) was heated to 80° C. for 2 hours. The mixture was cooled to ambient temperature and partitioned between diethyl ether and dilute aqueous sodium bicarbonate solution. The organic phase was washed with water and with a saturated aqueous sodium chloride solution, dried (MgSO$_4$) and evaporated. The residue was purified by column chromatography using increasingly polar mixtures of petroleum ether (b.p. 40°-60° C.) and methylene chloride as eluent. There was thus obtained 4-ethyl-2-methoxymethyl-4-[3-(naphth-2-ylmethoxy)phenyl]-1,3-dioxolane (1 g, 80%), as an oil and as a mixture of diastereoisomers.

NMR Spectrum 0.8(t, 3H), 1.7-2.2(m, 2H), 3.25-3.65(m, 5H), 3.9-4.1(m, 2H), 5.1(2 t's, 1H), 5.25(s, 2H), 6.75-8.0(m, 11H).

EXAMPLE 4

The procedure described in Example 3 was repeated except that 4-methoxybutan-2-one dimethyl acetal was used in place of 2-methoxyacetaldehyde dimethyl acetal. There was thus obtained 4-ethyl-2-(2-methoxyethyl)-2-methyl-4-[3-(naphth-2-ylmethoxy)phenyl]-1,3-dioxolane in 83% yield, as an oil and as a mixture of diastereoisomers.

NMR Spectrum (CDCl$_3$, delta values) 0.7-0.86(2 t's, 3H), 1.25 and 1.51(2 s's, 3H), 1.52-2.2(m, 4H), 3.25 and 3.35(2 s's, 3H), 3.4 and 3.61(2 d's, 2H), 4.08(s, 2H), 5.23(s, 2H), 6.75-8.0(m, 11H).

EXAMPLE 5

Concentrated sulphuric acid (5 drops) was added to a solution of 2-hydroxy-2-[3-(naphth-2-ylmethoxy)-phenylpropionaldehyde dimethyl acetal (1.5 g) in acetone (30 ml) and the mixture was stirred at ambient temperature for 5 hours. A saturated aqueous sodium bicarbonate solution (30 ml) was added and the bulk of the acetone was evaporated. The residue was partitioned between diethyl ether and water. The organic phase was washed with water and with a saturated sodium chloride solution, dried (MgSO$_4$) and evaporated. The residue, comprising a mixture of diastereoisomers, was purified by column chromatography using increasingly polar mixtures of petroleum ether (b.p. 40°-60° C.) and methylene chloride as eluent. There was thus obtained the less polar diastereoisomer, (4SR,5RS) -2,2,4-trimethyl-5-methoxy-4-3-(naphth-2-ylmethoxy)phenyl-1,3-dioxolane (0.39 g, 31%), m.p. 100°-103° C.; the 4-methyl and 5-methoxy groups being in a cis-relationship.

The 2-hydroxy-2-3-(naphth-2-ylmethoxy)phenylpropionaldehyde dimethyl acetal, used as a starting material, was obtained as follows:

Pyruvic aldehyde dimethyl acetal (0.665 ml) was added dropwise to a solution of 3-(napth-2-ylmethoxy)-phenylmagnesium bromide prepared by heating a mixture of 3-(naphth-2-ylmethoxy)bromobenzene (1.36 g), magnesium (0.12 g), a crystal of iodine and tetrahydrofuran (6 ml) in tetrahydrofuran. The mixture was stirred at ambient temperature for 1 hour. The mixture was partitioned between diethyl ether and a saturated aqueous ammonium chloride solution. The organic phase was washed with water and with a saturated aqueous sodium chloride solution, dried (MgSO$_4$) and evaporated. There was thus obtained the required starting material (1.8 g), as an oil which crystallised.

EXAMPLE 6

A mixture of 4-ethyl-4-(3-hydroxyphenyl)-2,2-dimethyl-1,3-dioxolane (1.0 g), 3-phenylprop-2-ynyl bromide (1.0 g), potassium carbonate (0.75 g) and dimethylformamide (10 ml) was stirred at ambient temperature for 15 hours. The mixture was partitioned between methylene chloride and water. The organic layer was washed with water, dried (MgSO$_4$) and evaporated. The residue was purified by column chromatography using a 4:1 v/v mixture of methylene chloride and petroleum ether as eluent. There was thus obtained 4-ethyl-2,2-dimethyl-4-3-(3-phenylprop-2-ynyloxy)phenyl -1,3-dioxolane (1.16 g, 77%), as an oil.

NMR Spectrum (CDCl$_3$, delta values) 0.79(t, 3H), 1.33(s, 3H), 1.51(s, 3H), 1.80(q, 2H), 4.08(s, 2H), 4.91(s, 2H), 6.6-7.5(m, 9H).

The 4-ethyl-4-(3-hydroxyphenyl)-2,2-dimethyl-1,3-dioxolane, used as a starting material, was obtained as follows:

The procedure described in the portion of Example 1 which is concerned with the preparation of starting materials was repeated except that benzyl bromide was used in place of 2-bromomethylnaphthalene. There was thus obtained 2-(3-benzyloxyphenyl)butane-1,2-diol in 42% yield.

The product so obtained was reacted with acetone using the procedure described in Example 1 to give 4-(3-benzyloxyphenyl)-4-ethyl-2,2-dimethyl-1,3-dioxolane in 89% yield, m.p. 51°-53° C.

A mixture of the product so obtained (3.3 g), 10% palladium-on-charcoal catalyst (0.4 g) and ethanol (50 ml) was stirred under an atmosphere of hydrogen for 5 hours. The mixture was filtered and the filtrate was evaporated. There was thus obtained the required starting material (1.7 g, 70%), as an oil which was used without further purification.

EXAMPLE 7

The procedure described in Example 6 was repeated using the appropriate alkyl halide and the appropriate phenol. There were thus obtained the compounds described in the following table:

TABLE II

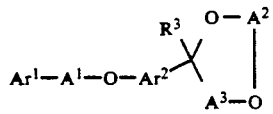

| Ex. 7 Compd. No. | Ar¹—A¹— | Ar² | R³ | A² | A³ | m.p. (°C.) | Yield (%) |
|---|---|---|---|---|---|---|---|
| 1ᵃ | 3-phenylprop-2-ynyl | 1,3-phenylene | CH$_2$OMe | C(Me)$_2$ | CH$_2$ | oil | 55 |
| 2ᵇ | naphth-2-ylmethyl | 5-fluoro-1,3-phenylene | Me | C(Me)$_2$ | CH(Me) | oil | 89 |
| 3ᶜ | 3-phenylprop-2-ynyl | 5-fluoro-1,3-phenylene | Me | C(Me)$_2$ | CH(Me) | oil | 45 |
| 4ᵈ | 7-fluoronaphth-2-ylmethyl | 5-fluoro-1,3-phenylene | Et | C(Me)$_2$ | CH$_2$ | oil | 73 |
| 5ᵉ | 7-methylnaphth-2-ylmethyl | 5-fluoro-1,3-phenylene | Et | C(Me)$_2$ | CH$_2$ | oil | 91 |
| 6ᶠ | 7-fluoronaphth-2-ylmethyl | 5-fluoro-1,3-phenylene | Et | CH(Et) | CH$_2$ | oil | 93 |
| 7ᵍ | 7-fluoronaphth-2-ylmethyl | 1,3-phenylene | Me | C(Me)(Pr$^n$) | CH$_2$ | oil | 61 |
| 8ʰ | 7-fluoronaphth-2-ylmethyl | 1,3-phenylene | Me | C(Me)(Pr$^n$) | CH$_2$ | oil | 79 |
| 9ⁱ | 7-methylnaphth-2-ylmethyl | 1,3-phenylene | Me | C(Me)(Pr$^n$) | CH$_2$ | oil | 54 |
| 10ʲ | 7-methylnaphth-2-ylmethyl | 1,3-phenylene | Me | C(Me)(Pr$^n$) | CH$_2$ | oil | 80 |

NOTES a. The product displayed the following characteristic NMR signals (CDCl$_3$, delta values) 1.36(s, 3H), 1.55(s, 3H), 3.33(s, 3H), 3.53(m, 2H), 4.93(q, 2H), 4.93(s, 2H), 6.8–7.5(m, 9H).

The 4-(3-hydroxyphenyl)-4-methoxymethyl-2,2-dimethyl-1,3-dioxolane, used as a starting material, was obtained as follows:

Methoxyacetonitrile (14 g) in tetrahydrofuran (10 ml) was added to a solution of 3-benzyloxyphenylmagnesium bromide [prepared by heating a mixture of 3-benzyloxybromobenzene (52.6 g), magnesium powder (4.8 g) and tetrahydrofuran (250 ml) to 60° C. for 3 hours] in tetrahydrofuran and the mixture was heated to 60° C. for 30 minutes. The mixture was cooled to ambient temperature and acidified by the addition of 3N hydrochloric acid solution (250 ml). The mixture was extracted with diethyl ether. The organic phase was washed with water and with a saturated aqueous sodium chloride solution, dried (MgSO$_4$) and evaporated. The residue was purified by column chromatography using a 19:1 v/v mixture of methylene chloride and diethyl ether as eluent. There was thus obtained 3-benzyloxyphenyl methoxymethyl ketone (32.3 g, 63%), as an orange oil.

Using the procedure described in the second and third paragraph of the portion of Example 1 which is concerned with the preparation of starting materials, a portion (10 g) of the ketone so obtained was reacted with isopropoxydimethylsilylmethylmagnesium chloride and the product so obtained was oxidised with hydrogen peroxide. There was thus obtained 2-(3-benzyloxyphenyl)-3-methoxypropane-1,2-diol (9.04 g, 80%), as an oil.

Using the procedure described in Example 1, a portion (0.837 g) of the product so obtained was reacted with acetone to give 4-(3-benzyloxyphenyl)-4-methoxymethyl-2,2-dimethyl-1,3-dioxolane, as an oil, and, using the procedure described in the last paragraph of Example 6 which is concerned with the preparation of starting materials the product so obtained was hydrogenolysed. There was thus obtained the required starting material (0.52 g, 75%), as an oil.

b. The product obtained was the (4RS,5RS)-isomer or threo-isomer, i.e. the 4- and 5-methyl groups were in a cis relationship. The product displayed the following characteristic NMR signals (CDCl$_3$, delta values) 1.25–1.5(m, 12H), 3.95(q, 1H), 5.2(s, 2H), 6.5–8.0(m, 10H).

The (4RS,5RS)-4-(5-fluoro-3-hydroxyphenyl)-2,2,4,5-tetramethyl-1,3-dioxolane, used as a starting material, was obtained as follows:

A mixture of benzyl alcohol (10 g), sodium hydride (4.44 g of a 50% w/w dispersion in mineral oil) and dimethylacetamide (180 ml) was stirred at ambient temperature for 1 hour; 1-bromo -3,5-difluorobenzene (10.65 ml) was added and the exothermic reaction mixture was stirred for 2 hours. The mixture was evaporated and the organic layer was separated, washed with water, dried (MgSO$_4$) and evaporated. The residue was purified by column chromatography using a 0:1 v/v mixture of petroleum ether (b.p. 60°-80° C.) and ethyl acetate as eluent. There were thus obtained, as a liquid, benzyl 3-bromo-5-fluorophenyl ether (19.5 g, 75%).

A solution of 3-tert-butyldimethylsilyloxybutan-2-one (5.56 g; prepared by reacting 3-hydroxybutan-2-one with tert-butyldimethylsilyl chloride in diethyl ether and using imidazole as a suitable base) in tetrahydrofuran (5 ml) was added to a solution of 3-benzyloxy-5-fluorophenylmagnesium bromide [prepared by heating a mixture of benzyl 3-bromo-5-fluorophenyl ether (6.7 g), magnesium powder (0.58 g) and tetrahydrofuran (50 ml) to 40° C. for 1 hour] in tetrahydrofuran (50 ml) and the mixture was stirred at ambient temperature for 2.5 hours. The mixture was evaporated and the residue was partitioned between diethyl ether and water. The organic phase was washed with a saturated aqueous sodium chloride solution, dried (MgSO$_4$) and evaporated. The residue was purified by column chromatography using a 3:2 v/v mixture of petroleum ether (b.p. 40°-60° C.) and methylene chloride as eluent. There was thus obtained an erythro isomer, (2RS,3SR)-2-(3-benzyloxy-5-fluorophenyl)-3-(tert-butyldimethylsilyloxybutan -2-ol (3.8 g, 41%), as an oil; and a threo isomer, the corresponding (2RS,3RS)-isomer (1.73 g, 18%), as an oil.

After appropriate repetition of the above reactions, a mixture of the threo-isomer so obtained (2.15 g), tetrabutylammonium fluoride (1M solution in tetrahydrofuran, 8.2 ml) and tetrahydrofuran (20 ml) was stirred at ambient temperature for 15 hours. The mixture was evaporated and the residue was partitioned between methylene chloride and water. The organic phase was washed with water, dried (MgSO$_4$) and evaporated. The residue was purified by column chromatography using a 7:3 v/v mixture of methylene chloride and diethyl ether as eluent. There was thus obtained (2RS,3RS)-2-(3-benzyloxy-5-fluorophenyl)butane-2,3-diol (1.43 g, 90%), as an oil.

Using the procedure described in Example 1, the product so obtained was reacted with acetone to give a dioxolane which, using the procedure described in the last paragraph of the portion of Example 6 which is concerned with the preparation of starting materials, was hydrogenolysed to give the required starting material (0.95 g, 74%), as an oil.

c. The product was a (4RS,5RS)-isomer or threo-isomer i.e. the 4- and 5-groups were in a cis-relationship. The product displayed the following characteristic NMR signals (CDCl$_3$, delta values) 1.25–1.53(m, 12H), 4.0(q, 1H), 4.9(s, 2H), 6.5–7.0(m, 3H), 7.2–7.5(m, 5H).

d. The product displayed the following characteristic NMR signals (CDCl$_3$, delta values) 0.78(t, 3H), 1.29(s, 3H), 1.52(s, 3H), 1.7–2.0(m, 2H), 4.05(s, 2H), 5.2(s, 2H), 6.5–6.9(m, 3H), 7.1–7.6(m, 3H), 7.7–8.0(m, 3H).

The 4-ethyl-4-(5-fluoro-3-hydroxyphenyl) -2,2-dimethyl-1,3-dioxolane, used as a starting material, was obtained as follows:

The process described in the second paragraph of the portion of Note b. above which is concerned with the preparation of starting materials was repeated except that 1-trimethylsilyloxybutan-2-one (prepared by reacting 1-hydroxybutan-2-one with trimethylsilyl chloride in diethyl ether and using triethylamine as a suitable base) was used in place of 3-tert-butyldimethylsilyloxybutan-2-one. The product so obtained was treated with tetrabutyl ammonium fluoride using the procedure described in Note b. above. There was thus obtained 2-(3-benzyloxy-5-fluorophenyl)butane-1,2-diol in 46% overall yield, as an oil.

Using the procedure described in Example 1, a portion (1.36 g) of the product so obtained was reacted with acetone to give a dioxolane which, using the procedure described in the portion of Example 6 which is concerned with the preparation of starting materials, was hydrogenolysed to give the required starting material (1.02 g, 85%), as an oil.

e. The product displayed the following characteristic NMR signals CDCl$_3$, delta values) 0.79(t, 3H), 1.3(s, 3H), 1.5 s, 3H), 1.7–2.0(m, 2H), 2.51(s, 3H), 4.04(m, 2H), 5.18(s, 2H), 6.5–7.9(m, 9H).

f. The product was obtained as a mixture of diastereoisomers. The product mixture displayed the following characteristic NMR signals (CDCl$_3$, delta values) 0.6–1.1(2 t's, 6H), 1.5–2.0(m, 4H), 3.95(q, 2H), 5.1(t, 1H), 5.19(s, 2H), 6.5–8.0(m, 9H).

The 2,4-diethyl-4-(5-fluoro-3-hydroxyphenyl) -1,3-dioxolane, used as a starting material, was obtained as follows:

Using the procedure described in Example 1, 2-(3-benzyloxy-5-fluorophenyl)butane-1,2-diol (1.02 g) was reacted with propionaldehyde (6 ml) in the presence of concentrated sulphuric acid (1 drop) to give 4-(3-benzyloxy-5-fluorophenyl)-2,4-diethyl-1,3-dioxolane, as an oil and as a mixture of diastereoisomers. The product so obtained was hydrogenolysed using the procedure described in the Portion of Example 6 which is concerned with the preparation of starting materials. There was thus obtained the required starting material (0.5 g, 60%), as an oil.

g. The product displayed an optical rotation $[\alpha]^{20} = +4.8°$ (chloroform, c = 1.034 g/100 ml), and the following characteristic NMR signals (CDCl$_3$, delta values) 0.86(t, 3H), 1.15–1.75(m, 10H), 4.05(s, 2H), 5.22(s, 2H), 6.75–8.0(m, 10H).

The (+)-4-(3-hydroxyphenyl)-2,4-dimethyl-2-n-propyl-1,3-dioxolane, used as a starting material, was obtained from (+)-2,4-dimethyl-4-[3-(naphth-2-ylmethoxy)phenyl]-2-n-propyl-1,3-dioxolane (Ex. 2, Compound No. 13; 0.66 g) by hydrogenolysis of an ethanolic solution for 7 hours under an atmosphere of hydrogen. The phenol was obtained as an oil (0.3 g, 72%) and displayed an optical rotation, $[\alpha]^{20} = +10.4°$ (chloroform, c = 1.204 g/100 ml).

h. The product displayed an optical rotation, $[\alpha]^{20} = -4.7$ (chloroform, c = 1.011 g/100 ml), and the same characteristic NMR signals given in Note g. above.

The (−)-4-(3-hydroxyphenyl)-2,4-dimethyl-2-n-propyl-1,3-dioxolane, used as a starting material, was obtained from (−)-2,4-dimethyl-4-[3-(naphth-2-ylmethoxy)phenyl]-2-n-propyl-1,3-dioxolane (Ex. 2, Compound No. 14) by hydrogenolysis. The phenol was obtained as an oil in 96% yield, and displayed an optical rotation, $[\alpha]^{20} = -10.7°$ (chloroform, c = 1.027 g/100 ml).

i. The product displayed an optical rotation, $[\alpha]^{20} = +5.94°$ (chloroform, c = 1.01 g/100 ml), and the following characteristic NMR signals (CDCl$_3$, delta values) 0.85(t, 3H), 1.15–1.75(m, 10H), 2.5(s, 3H), 4.05(s, 2H), 5.2(s, 2H), 6.75–7.95(m, 10H).

j. The product displayed an optical rotation, $[\alpha]^{20} = -6.09$ (chloroform, c = 1.02 g/100 ml) and the same characteristic NMR signals given in Note i. above.

Information concerning the preparation of appropriate starting materials for the compounds described within Example 7 is provided below: i) The procedure used to prepare the appropriate 2-bromomethylnaphthalenes for use in the preparation of compounds Nos 4 to 6 is illustrated below by the description of the preparation of 2-bromomethyl-7-fluoronaphthalene. The other 2-bromomethylnaphthalenes were prepared in analogous fashion. Thus:

A mixture of 7-fluoro-2-methylnaphlhalene (3. 0 g,) N-bromosuccinimide (3.3 g), 2,2'-azobisisobutyronitrile (0.2 g) and carbon tetrachloride (100 ml) was heated to reflux and irradiated with the light from a 275 watt bulb for 1 hour. The mixture was cooled to ambient temperature and filtered. The filtrate was evaporated and the residue was purified by column chromatography using a 19:1 v/v mixture of petroleum ether (b.p. 60°–80° C.) and toluene as eluent. There was thus obtained 2-bromomethyl-7-fluoronaphthalene (2.8 g , m.p. 62° C.

The procedure described immediately above was repeated except that the appropriate 2-methylnaphthalene was used in place of 7-fluoro-2-methylnaphthalene and the reaction product was purified by column chromatography using increasingly polar mixtures of petroleum ether (b.p. 60°–80° C.) and toluene as eluent. There were thus obtained the 2-bromomethylnaphthalenes listed below:

2-bromomethyl-7-methylnaphthalene, m.p. 100° C.

NOTES

2-Methyl-7-fluoronaphthalene used as a starting material was obtained as follows:

3-Fluorobenzyl chloride was reacted with acetylacetaldehyde dimethyl acetal using the procedure described for the corresponding reaction of 3-methylbenzyl chloride (Synthesis, 1974, 566). There was thus obtained 4-(3-fluorophenyl)-3-hydroxy -3-methylbutanal dimethyl acetal (b.p. 125°–135° C. at 0.25 mm Hg).

A mixture of the material so obtained (15 g), glacial acetic acid (60 ml) and hydrobromic acid (48% w/v, 48 ml) was heated on a steam bath for 1 hour. The mixture was evaporated and the residue was purified by column chromatography using petroleum ether (b.p. 60°-80° C.) as eluent. There were thus obtained 7-fluoro-2-methylnaphthalene (4 g).

EXAMPLE 8

Using the procedure described in Example 1, 2-[3-(naphth-2-ylmethoxy)phenyl]-4-(2,5,5-trimethyl-1,3-dioxan-2-yl)butane-1,2-diol (0.77 g) was reacted with acetone to give 4-(2-acetylethyl)-2,2-dimethyl -4-[3-(naphth-2-ylmethoxy)phenyl]-1,3-dioxolane (0.32 g, 45%), as an oil.

NMR Spectrum (CDCl$_3$, delta values) 1.32(s, 3H), 1.55(s, 3H), 2.0(s, 3H), 2.05-2.6(m, 4H), 4.1(q, 2H), 5.25(s, 2H), 6.75-8.0(m, 11H).

The 2-[3-(naphth-2-ylmethoxy)phenyl]-4-(2,5,5-trimethyl-1,3-dioxan-2-yl)butane-1,2-diol, used as a starting material, was obtained as follows:

Using he procedure described in the second and third paragraphs of the portion of Example 1 which is concerned with the preparation of starting materials, 3-(naphth-2-ylmethoxy) benzaldehyde [prepared by the alkylation of 3-hydroxybenzaldehyde with 2-bromomethylnaphthalene using dimethylformamide as the reaction solvent and potassium carbonate as a suitable base was treated with isopropoxydimethylsilylmethylmagnesium chloride and the product so obtained was oxidised. There was thus obtained 2-[3-(naphth-2-ylmethoxy)phenyl]ethane-1,2-diol, m.p. 121°-122° C.

A mixture of the diol (17.1 g) so obtained, tert-butyldimethylsilyl chloride (9.6 g), imidazole (4.35 g) and dimethylformamide (50 ml) was stirred at ambient temperature for 48 hours. The mixture was partitioned between ethyl acetate and water. The organic layer was washed with water, dried (MgSO$_4$) and evaporated. The residue was purified by column chromatography using methylene chloride as eluent. There was thus obtained 1-tert -butyldimethylsilyloxy-2-[3-(naphth-2-ylmethoxy)phenylethan-2-ol (17.8 g, 75%), m.p. 66°-67° C.

A mixture of a portion (7.65 g) of the alcohol so obtained, manganese dioxide (90 g) and acetone (200 ml) was stirred at ambient temperature for 48 hours. The mixture was filtered and the filtrate was evaporated. The residue was purified by column chromatography using methylene chloride as eluent. There was thus obtained tert-butyldimethylsilyloxymethyl 3-(naphth-2-ylmethoxy)phenyl ketone (1.62 g, 21%), m.p. 67°-68° C.

A solution of the ketone so obtained in tetrahydrofuran (5 ml) was added to a solution of 2-(2,5,5-trimethyl-1,3-dioxan-2-yl)ethylmagnesium bromide prepared by heating a mixture of 2-(2,5,5-trimethyl-1,3-dioxan-2-yl)ethyl bromide (2.24 g), magnesium powder (0.682 g) and tetrahydrofuran (25 ml) to 40° C. for 30 minutes in tetrahydrofuran (25 ml) which had been cooled to ambient temperature. The mixture was stirred at ambient temperature for 1 hour and evaporated. The residue was partitioned between ethyl acetate and water. The organic phase was washed with water, dried (MgSO$_4$) and evaporated. The residue was purified by column chromatography using a 50:1 v/v mixture of methylene chloride and diethyl ether as eluent. There was thus obtained 1-tert-butyldimethylsilyloxy-2-[3-(napth-2-ylmethoxy)phenyl]-4-(2,5,5-trimethyl-1,3-dioxan-2-yl)butan-2-ol (2.14 g, 96%), as an oil.

A mixture of a portion (0.98 g) of the product so produced, tetrabutylammonium fluoride (1M in tetrahydrofuran, 5.2 ml) and tetrahydrofuran (3 ml) was stirred at ambient temperature for 15 hours. The mixture was evaporated and the residue was purified by column chromatography using a 9:1 v/v mixture of methylene chloride and acetone as eluent. There was thus obtained the required starting material (0.61 g, 78%), as an oil.

EXAMPLE 9

A mixture of 3-cyanomethoxyphenyl iodide (0.235 g), tetrakis(triphenylphosphine)palladium (0.052 g) and toluene (4 ml) was stirred at ambient temperature for 15 minutes. To this mixture there were added in turn 4-ethyl-4-[5-fluoro-3-(prop-2-ynyloxy)phenyl]-2,2-dimethyl-1,3-dioxolane (0.252 g), cuprous iodide (0.009 g) and piperidine (0.155 g). The mixture was stirred at 20° C. for 2 hours. The mixture was partitioned between toluene and water. The organic layer was washed with a saturated aqueous sodium chloride solution, dried (MgSO$_4$) and evaporated. The residue was purified by column chromatography using a 1:1 v/v mixture of petroleum ether (b.p. 40°-60° C.) and methylene chloride as eluent. There was thus obtained 4-[3-(3-(3-cyanomethoxy)phenylprop-2-ynyloxy)-5-fluorophenyl]-4-ethyl-2,2-dimethyl-1,3-dioxolane (0.28 g, 77%), as an oil.

NMR Spectrum (CDCl$_3$, delta values) 0.8(t, 3H), 1.3(s, 3H), 1.55(s, 3H), 1.75-2.05(m, 2H), 4.07(s, 2H), 4.75(s, 2H), 4.9(s, 2H), 6.5-7.5(m, 7H).

The 4-ethyl-4-[5-fluoro-3-(prop-2-ynyloxy)phenyl]-2,2-dimethyl -1,3-dioxolane, used as a starting material, was obtained as follows:

Using the procedure described in Example 6, 4-ethyl-4-(5-fluoro-3-hydroxyphenyl)-2,2-dimethyl-1,3-dioxolane was reacted with prop-2-ynyl bromide. There was thus obtained the required starting material in 87% yield, as an oil.

EXAMPLE 10

Using the procedure described in Example 1, 2-5-(3-phenylprop-2-ynyloxy)pyrid-3-yl]propane-1,2-diol was reacted with acetone to give 2,2,4-trimethyl-4-[5-(3-phenylprop-2-ynyloxy)pyrid-3-yl]-1,3-dioxolane in 76% yield, as an oil.

NMR Spectrum (CDCl$_3$, delta values) 1.4(s, 3H), 1.55(s, 3H), 1.6(s, 3H), 4.1(s, 2H), 4.95(s, 2H), 7.2-7.5(m, 6H), 8.2-8.3(m, 2H).

The 2-[5-(3-phenylprop-2-ynyloxy)pyrid-3-yl]propane-1,2-diol, used as a starting material, was obtained as follows:

3-Phenylprop-2-ynyl bromide (0.195 g) was added dropwise to a mixture of 3-bromo-5-hydroxypyridine (0.174 g; UK Patent Applic. No. 2025953), potassium carbonate (0.14 g) and dimethylformamide (5 ml) which had been cooled to −15° C. The mixture was partitioned between ethyl acetate and a saturated aqueous ammonium chloride solution. The organic phase was dried (MgSO$_4$) and evaporated. The residue was purified by column chromatography using methylene chloride as eluent. There was thus obtained 3-bromo-5-(3-phenylprop-2-ynyloxy)pyridine (0.14 g, 49%), as an oil.

NMR Spectrum (CDCl$_3$, delta values) 4.95(s, 2H), 7.25-8.1(m, 6H), 8.25-8.5(m, 2H).

After appropriate repetition of the above reaction the product so obtained was treated as follows:

n-Butyl-lithium (1.6M in hexane, 6.5 ml) was added dropwise to a solution of the product so obtained (2.88 g) in tetrahyhdrofuran (130 ml) which had been cooled to −110° C. The mixture was stirred at this temperature for 10 minutes and then 1-trimethylsilyloxypropan-2-one (1.5 g; prepared by reacting hydroxyacetone with trimethylsilyl chloride in diethyl ether and using triethylamine as a suitable base) was added dropwise. The mixture was allowed to warm to −10° C. over a period of 1 hour. The mixture was partitioned between diethyl ether and a saturated aqueous ammonium chloride solution. The organic phase was dried(MgSO$_4$) and evaporated and the residue was purified by column chromatography using 50:50:1 v/v mixture of methylene chloride, diethyl ether and methanol as eluent. The product so obtained was dissolved in ethyl acetate (15 ml) and shaken with 1N aqueous hydrochloric acid solution. The organic layer was washed with water, dried (MgSO$_4$) and evaporated. There was thus obtained the required starting material in 27% yield, as an oil.

NMR Spectrum (CDCl$_3$, delta values) 1.45(s, 3H), 3.5–4.0(m, 4H), 4.88(s, 2H), 7.1–7.6(m, 6H), 8.0–8.3(m, 2H).

EXAMPLE 11

Using the procedure described in Example 1, 2-[5-(3-phenylprop-2-ynyloxy)pyrid-3-yl]butane-1,2-diol was reacted with acetone to give 4-ethyl-2,2-dimethy-4-[5-(3-phenylprop-2-ynyloxy)pyrid-3-yl]-1,3-dioxolane in 59% yield, as an oil.

NMR Spectrum (CDCl$_3$, delta values) 0.75(s, 3H), 1.25(s, 3H), 1.45(s, 3H), 1.85(q, 2H), 3.95–4.25(m, 2H), 4.95(s, 2H), 7.1–7.4(m, 6H), 8.1–8.3(m, 2H).

The 2-[5-(3-phenylprop-2-ynyloxy)pyrid-3-yl]butane-1,2-diol, used as a starting material, was obtained by repeating the procedure described in the second paragraph of the portion of Example 10 which is concerned with the preparation of starting materials, except that 1-trimethylsilyloxybutan-2-one was used in place of 1-trimethylsilyloxypropan-2-one. There was thus obtained the required starting material in 37% yield, as an oil.

NMR Spectrum (CDCl$_3$, delta values) 0.76(t, 3H), 1.6–2.0(m, 2H), 3.5–3.95(m, 2H), 4.95(s, 2H), 7.1–7.55(m, 6H), 8.05–8.25(m, 2H).

EXAMPLE 12

Using the procedure described in Example 1, 2-[5-nitro-3-(3-phenylprop-2-ynyloxy)phenyl]propane-1,2-diol was reacted with acetone to give 2,2,4-trimethyl-4-[5-nitro-3-(3-phenylprop-2-ynyloxy)phenyl]-1,3-dioxolane in 95% yield, as an oil.

NMR Spectrum (CDCl$_3$, delta values) 1.38(s, 3H), 1.52(s, 3H), 1.59(s, 3H), 4.1(s, 2H), 5.0(s, 2H), 7.2–8.0(m, 8H).

The 2-[5-nitro-3-(3-phenylprop-2-ynyloxy)phenyl]propane-1,2-diol, used as a starting material, was obtained as follows:

A solution of 3-phenylprop-2-yn-1-ol (19 g) in dimethylacetamide (100 ml) was added to a stirred suspension of sodium hydride (50% w/w dispersion in mineral oil, 7.5 g) in dimethylacetamide (320 ml) and the mixture was stirred at ambient temperature for 1 hour. 1-iodo-3,5-dinitrobenzene (42 g; *J. Chem. Soc.* (C), 1970, 1480) was added to the mixture portionwise and the resultant mixture was stirred at ambient temperature for 2 hours. The mixture was partitioned between diethyl ether and 2N aqueous hydrochloric acid solution. The organic phase was washed with water, dried (MgSO$_4$) and evaporated. The residue was purified by column chromatography using increasingly polar mixtures of petroleum ether (b.p. 40°–60° C.) and methylene chloride as eluent. There was thus obtained 5-nitro-3-(3-phenylprop-2-ynyloxy)phenyl iodide (31 g, 58%), as an oil.

NMR Spectrum (CD$_3$SOCD$_3$, delta values) 5.25(s, 2H), 7.45(s, 5H), 7.9(m, 2H), 8.15(m, 1H).

A solution of a portion (2.6 g) of the product so obtained in tetrahydrofuran (100 ml) was cooled to −105° C. and n-butyl-lithium (1.2M in toluene; 4.3 ml) was added dropwise. The mixture was stirred at −100° C. for 10 minutes then 1-trimethylsilyloxypropan-2-one (1 g) was added dropwise. The mixture was stirred at −100° C. for 20 minutes. The mixture was allowed to warm to −30° C. and then a saturated aqueous ammonium chloride solution (30 ml) was added. The mixture was partitioned between diethyl ether and 2N aqueous hydrochloric acid solution. The organic phase was washed with water, dried (MgSO$_4$) and evaporated. The residue was purified by column chromatography using a 9:1 v/v mixture of methylene chloride and diethyl ether as eluent. There was thus obtained the required starting material in 50% yield, as an oil.

NMR Spectrum (CDCl$_3$, delta values) 1.55(s, 3H), 3.6–3.9(m, 2H), 5.0(s, 2H), 7.2–7.76(m, 6H), 7.85(m, 1H), 8.0(m, 1H).

EXAMPLE 13

A mixture of 2,2,4-trimethyl-4-[5-nitro-3 (3-phenylprop-2-ynyloxy)phenyl]-1,3-dioxolane (0.55 g), activated iron powder [2.6 g; obtained by stirring a mixture of iron powder and 2N hydrochloric acid for 10 minutes, filtering the mixture and washing and drying the solid], ferrous sulphate heptahydrate (0.26 g), triethylamine (100 ml), methanol (40 ml) and water (8 ml) was heated to 70° C. for 15 minutes. The mixture was cooled and filtered and the filtrate was evaporated. The residue was purified by column chromatography using a 3:2 v/v mixture of methylene chloride and diethyl ether as eluent. There was thus obtained 4-[5-amino-3-(3-phenylprop-2-ynyloxy)phenyl]-2,2,4-trimethyl-1,3-dioxolane (0.5 g, 99%), as an oil.

NMR Spectrum (CDCl$_3$, delta values) 1.26(s, 3H), 1.37(s, 3H), 1.42(s, 3H), 4.0(s, 2H), 4.85(s, 2H), 6.2–6.5(m, 3H), 7.1–7.5(m, 5H).

EXAMPLE 14

A mixture of 2-[3-methoxy-4-(napth-2-ylmethoxy)phenyl]butane-1,2-diol (0.39 g), acetone dimethyl acetal (0.5 g), p-toluenesulphonic acid (10 mg) and acetone (5 ml) was heated to reflux for 40 minutes. The mixture was evaporated and the residue was purified by column chromatography using increasingly polar mixtures of hexane and ethyl acetate as eluent. There was thus obtained 4-ethyl-4-[3-methoxy-4-(naphth-2-ylmethoxy)phenyl]-2,2-dimethyl -1,3-dioxolane (0.3 g, 69%), m.p. 86° C.

The 2-[3-methoxy-4-(naphth-2-ylmethoxy) phenyl]butane-1,2-diol, used as a starting material, was obtained as follows:

Using the procedure described in the first paragraph of Example 1 which is concerned with the preparation of starting materials, 2-bromomethylnaphthalene was reacted with 4-bromo -2-methoxyphenol to give 3- methoxy-4-(naphth-2-ylmethoxy)bromobenzene (62%), m.p. 108° C.

n-Butyl-lithium (1.4M in hexane, 3.2 ml) was added dropwise to a solution of the product so obtained (1.44 g) in tetrahydrofuran (35 ml) which had been cooled to −78° C. The mixture was stirred at this temperature for 5 minutes and then a solution of 1-(tert-butyldimethylsilyloxy)butan-2-one (0.85 g) in tetrahydrofuran (4 ml) was added. The mixture was stirred at −78° C. for 30 minutes and then allowed to warm to 0° C. The mixture was partitioned between diethyl ether and water. The organic phase was washed with water and with a saturated aqueous sodium chloride solution, dried ($MgSO_4$) and evaporated. The residue was purified by column chromatography using increasingly polar mixtures of hexane and ethyl acetate as eluent. There was thus obtained 1-(tert-butyldimethylsilyloxy)-2-[3-methoxy-4-(naphth-2-ylmethoxy)phenylbutan-2-ol (0.88 g, 45%), as an oil.

NHR Spectrum ($CDCl_3$, delta values) −0.07(s, 3H), 0.0(s, 3H), 0.76(t, 3H), 0.84(s, 9H), 1.64–1.96(m, 2H), 2.75–2.86(m, 1H), 3.64(s, 2H), 3.92(s, 3H), 5.3(s, 2H), 6.77(m, 1H), 6.88(m, 1H), 7.05(d, 1H), 7.4–7.9(m, 7H).

A mixture of the product so obtained, potassium fluoride (0.4 g) and dimethylformamide (2 ml) was heated to 100° C. for 40 minutes. The mixture was cooled to ambient temperature and tetrabutylammonium fluoride (1M in tetrahydrofuran, 2 ml) was added. The mixture was stirred at ambient temperature for 30 minutes. The mixture was partitioned between diethyl ether and water. The organic phase was washed with water, dried ($MgSO_4$) and evaporated. The residual solid was recrystallised from ethyl acetate to give 2-[3-methoxy-4-(naphth-2-ylmethoxy)phenylbutane-1,2-diol (0.4 g, 61%), m.p. 120° C.

EXAMPLE 15

Using a similar procedure to that described in Example 3, a mixture of 2-3-(naphth-2-ylmethoxy)phenylbutane-1,2-diol, isobutyraldehyde, p-toluenesulphonic acid and toluene was heated to 80° C. for 30 minutes. There were thus obtained 4-ethyl-2-isopropyl-4-[3-(naphth-2-ylmethoxy)phenyl-1,3-dioxolane (75%), as an oil and as a 3:1 mixture of less polar and more polar diastereoisomers.

NMR Spectrum ($CDCl_3$ delta values) 0.78 and 0.80(2 t s, 3H), 0.96 and 1.02(2 d's, 6H), 1.6–2.0(m, 3H), 3.95 and 3.99(s and d of d's, 2H), 4.68 and 4.84(2 d's, 1H), 5.23(s, 2H), 6.75–8.0(m, 11H).

Using a similar procedure to that described in Example 1, a mixture of 2-3-(naphth-2-ylmethoxy)phenylbutane-1,2-diol, isobutyraldehyde and concentrated sulphuric acid (1 drop) was stirred at ambient temperature for 4 hours. There was thus obtained 4-ethyl-2-isopropyl-4-[3-(naphth-2-ylmethoxy)phenyl 1,3-dioxolane (66%), as an oil and as a 4:1 mixture of more polar and less polar diastereoisomers.

NHR Spectrum ($CDCl_3$, delta values) 0.7–1.25(m, 9H), 1.5–2.0(m, 3H), 3.95(s, 2H), 4.7 and 4.85(2 d's, 1H), 5.25(s, 2H), 6.75–8.0(m, 11H).

EXAMPLE 16

Using a similar procedure to that described in Example 3, a mixture of 2-[3-(naphth-2-ylmethoxy)phenyl]butane -1,2-diol, isovaleraldehyde, p-toluenesulphonic acid and toluene was heated to 80° C. for 30 minutes. There was thus obtained 4-ethyl-2-isobutyl-4-[3-(naphth-2-ylmethoxy)phenyl]-1,3-dioxolane (82%), as an oil and as a 1 mixture of less polar and more polar diastereoisomers.

NMR Spectrum ($CDCl_3$, delta values) 0.78 and 0.80(2 t's, 3H), 0.93 and 1.0(2 s's, 6H), 1.5–2.0(m, 5H), 3.8–4.1(m, 2H), 5.02 and 5.21(2 t's, 1H), 5.233(s, 2H), 6.75–8.0(m, 11H).

Using a similar Procedure to that described in Example 1, a mixture of 2-[3-(naphth-2-ylmethoxy)phenyl]butane-1,2-diol, isovaleraldehyde and concentrated sulphuric acid (1 drop) was stirred at ambient temperature for 5 hours. There was thus obtained 4-ethyl-2-isobutyl-4-[3-(naphth-2-ylmethoxy)phenyl-1,3-dioxolane (77%), as an oil and as a 4:1 mixture of more polar and less polar diastereoisomers.

NMR Spectrum ($CDCl_3$, delta values) 0.7–1.1(m, 9H), 1.5–2.1(m, 5H), 3.8–4.1(m, 2H), 5.0 and 5.2(2 t's, 1H), 5.25(s, 2H), 6.75–8.0(m, 11H).

EXAMPLE 17

Using a similar procedure to that described in Example 3, a mixture of 2-[3-(naphth-2-ylmethoxy)phenyl]butan -1,2-diol, butyraldehyde, p-toluenesulphonic acid and toluene was stirred at ambient temperature for 66 hours. There was thus obtained 4-ethyl-4-[3-(naphth-2-ylmethoxy)phenyl]-2-propyl-1,3-dioxolane (93 %), as an oil and as a 4:1 mixture of less polar and more polar diastereoisomers.

NMR Spectrum ($CDCl_3$, delta values) 0.6–1.01(m, 6H), 1.15–2.0(m, 6H), 4.06(d of d's, 2H), 4.92 and 5.16(2 t's, 1H), 5.23(s, 2H), 6.75–8.0(m, 11H).

EXAMPLE 18

A mixture of 2-[3-(7-fluoronaphth-2-ylmethoxy)phenyl pent-4-ene-1,3-diol (0.44 g), 2-methoxypropene (0.36 g), p-toluenesulphonic acid (0.02 g) and N,N-dimethylformamide (8 ml) was heated to 60° C. for 3 hours. The mixture was partitioned between diethyl ether and water. The organic layer was washed with a saturated aqueous sodium bicarbonate solution and with a saturated aqueous sodium chloride solution, dried ($MgSO_4$) and evaporated. The residue was purified by column chromatography using a 50:1 v/v mixture of methylene chloride and diethyl ether as eluent. There was thus obtained 2,2-dimethyl-4-[3-(7-fluoronaphth-2-ylmethoxy)phenyl-4-(prop-2-enyl)-1,3-dioxolane (0.43 g, 88%), as an oil.

NMR Spectrum ($CDCl_3$, delta values) 1.27(s, 3H), 1.53(s, 3H), 2 57(d, 2H), 4.1(q, 2H), 4.89–4.9(m, 1H), 5.06–5.07(m, 1H), 5.22(s, 2H), 5.5–6.0(s, 1H), 6.8–8.0(m, 10H).

The 2-3-(7-fluoronaphth-2-ylmethoxy)phenyl]pent-4-ene-1,3-diol, used as a starting material, was obtained as follows:

A mixture of bromomethyl 3-hydroxyphenyl ketone (1.4 g; J. Org. Chem., 1969, 3459), sodium bicarbonate (2.65 g), water (5 ml) and ethanol (15 ml) was heated to reflux for 4 hours. The mixture was partitioned between ethyl acetate and water. The organic layer was washed with a saturated aqueous sodium chloride solution, dried ($MgSO_4$) and evaporated. The residue was purified by column chromatography using a 9:1 v/v mixture of methylene chloride and acetone as eluent. There was thus obtained hydroxymethyl-1,3-hydroxyphenyl ketone (0.62 g, 62%), as an oil.

After appropriate repetition of the above-described reaction, a mixture of the product so obtained (6.08 g), tert-butyldimethylsilyl chloride (18.1 g), imidazole (13.6 g) and N,N-dimethylformamide (80 ml) was stirred at ambient temperature for 15 hours. The mixture was partitioned between dethyl ether and water. The organic phase was washed with a saturated aqueous sodium chloride solution, dried (MgSO₄) and evaporated. There was thus obtained tert-butyldimethylsilyloxymethyl 3-tert-butyldimethylsilyloxyphenyl ketone (18.3 g) as an oil, which was used without further purification.

A mixture of a portion (3.81 g) of the product so obtained, allyl bromide (4.22 g), magnesium powder (0.84 g) and tetrahydrofuran (30 ml) was heated to reflux for 5 minutes and then stirred at ambient temperature for 5 hours. The mixture was evaporated and the residue was partitioned between diethyl ether and water. The organic phase was washed with a saturated aqueous ammonium chloride solution, dried (MgSO₄) and evaporated. The residue was purified by column chromatography using a 10:3 v/v mixture of petroleum ether (b.p. 40°-60° C.) and methylene chloride as eluent. There was thus obtained 1-tert-butyldimethylsilyloxy -2-(3-tert-butyldimethylsilyloxyphenyl)pent-4-en-2-ol (1.1 g, 26%), as an oil.

Using the procedure described in the third paragraph of the portion of Note b. below Table II in Example 7, the product so obtained was reacted with tetrabutylammonium fluoride. There was thus obtained 2-(3-hydroxyphehyl)pent-4-ene-1,2-diol (0.3 g, 59%), as an oil.

Using the procedure described in Example 6, the product so obtained was alkylated with 2-bromomethyl-7-fluoronaphthalene. There was thus obtained the required starting material (0.44 g, 80%), as an oil.

EXAMPLE 19

A mixture of 2,2-dimethyl-4-[3-(7-fluoronaphth-2-ylmethoxy)phenyl]-4-(prop-2-enyl)-1,3-dioxolane (0.13 g), palladium-on-calcium carbonate (0.015 g) and methanol (3 ml) was stirred under an atmosphere of hydrogen for 15 minutes. The mixture was filtered and the filtrate was evaporated The residue was purified by column chromatography using methylene chloride as eluent. There was thus obtained 2,2-dimethyl-4-[3-(7-fluoronaphth -2-ylmethoxy)phenyl-4-propyl-1,3-dioxolane (0.13 g, 88%).

NMR Spectrum (CDCl₃, delta values) 0.8(t, 3H), 1.28(s, 3H), 1.5(s, 3H), 1.7-2.0(m, 4H), 4.07(s, 2H), 5.22(s, 2H), 6.75-8.0(m, 10H).

EXAMPLE 20

Using the procedure described in Example 6, (E)-cinnamyl bromide was reacted with 4-ethyl-4-(5-fluoro-3-hydroxyphenyl)-2,2-dimethyl-1,3-dioxolane to give 4-[3-((E)-cinnamyloxy)-5-fluorophenyl]-4-ethyl-2,2-dimethyl-1,3-dioxolane in 2% yield, as an oil.

NHR Spectrum (CDCl₃, delta values) 0.78(t, 3H), 1.33(s, 3H), 1.7-2.14(m, 2H), 4.05(s, 2H), 4.65-4.7(d of d's, 2H), 6.2-6.83(m, 5H), 7.26-7.55(m, 5).

EXAMPLE 21

Using the procedure described in Example 6, (+)-4-ethyl-4-(5-fluoro-3-hydroxyphenyl)-2,2-dimethyl-1,3-dioxolane was reacted with 2-bromomethyl-7-fluoronaphthalene. There was thus obtained (+)-4-ethyl-4-5-fluoro-3-(7-fluoronaphth-2-ylmethoxy)phenyl-2,2-dimethyl -1,3-dioxolane in 81% yield, m.p. 49°-50° C., $[\alpha]^{20} = +13.5$ (chloroform, c=1 g/100 ml).

The (+)- and (−)-4-ethyl-4-(5-fluoro-3-hydroxyphenyl)-2,2-dimethyl-1,3-dioxolanes, used as starting materials for Examples 21 and 22 respectively were obtained as follows:

A mixture of 2-oxobutyric acid (21 g), sec-butanol (32 ml) and p-toluenesulphonic acid (5.25 g) was stirred at ambient temperature for 75 hours. The mixture was partitioned between diethyl ether and water. The organic phase was dried (MgSO₄) and evaporated. There was thus obtained sec-butyl 2-oxobutyrate (16.1 g, 50%).

The product so obtained (15 g) was added dropwise to a solution of 3-benzyloxy-5-fluorophenylmagnesium bromide [prepared by heating a mixture of benzyl 3-bromo-5-fluorophenyl ether (31 g), magnesium powder (2.46 g) and diethyl ether (150 ml) to reflux for 1 hour] in diethyl ether and the mixture was stirred at ambient temperature for 15 hours. The mixture was partitioned between diethyl ether and a saturated aqueous ammonium chloride solution. The organic layer was washed with water, dried (MgSO₄) and evaporated. The residue was purified by column chromatography using a 3:1 v/v mixture of methylene chloride and petroleum ether as eluent. There was thus obtained sec-butyl 2-(3-benzyloxy-5-fluorophenyl)-2-hydroxybutyrate (16.3 g, 42%), as an oil.

A mixture of a portion (10 g) of the product so obtained, potassium carbonate (5.4 g), water (5 ml) and methanol (42 ml) was heated to 80° C. for 4 hours. The mixture was evaporated and the residue was partitioned between diethyl ether and water. The aqueous phase was acidified by the addition of concentrated hydrochloric acid and extracted with ethyl acetate. The organic layer was dried (MgSO₄) and evaporated. There was thus obtained 2-(3-benzyloxy 5-fluorophenyl)-2-hydroxybutyric acid (7.1 g, 84%), m.p. 105°-106° C.

A mixture of a portion (8.5 g) of the acid so obtained, quinine (9.07 g) and ethanol (100 ml) was stirred at ambient temperature for 30 minutes. The mixture was evaporated to leave the salt as a white solid. This material was dissolved in hot ethanol (28 ml), diisopropyl ether (230 ml) was added and the solution was allowed to stand at ambient temperature for 75 hours. The precipitated solid (7.13 g) was filtered off, dissolved in hot ethanol (35 ml) and then diisopropyl ether (300 ml) was added. The solution was allowed to stand at ambient temperature for 15 hours. The precipitate (4.93 g) was filtered off. The salt so obtained was dissolved in 2N aqueous hydrochloric acid solution and the solution was extracted with diethyl ether. The organic phase was washed with a saturated aqueous sodium chloride solution, dried (MgSO₄) and evaporated. There was thus obtained (−)-2-(3-benzyloxy-5-fluorophenyl) -2-hydroxybutyric acid (2.24 g).

The mother liquors from the crystallisation steps described immediately above were combined and evaporated to give the crude quinine salt (13.5 g). This salt was dissolved in 2N aqueous hydrochloric acid solution and extracted with diethyl ether. The organic phase was dried (MgSO₄) and evaporated. There was thus obtained crude (−)-2-(3-benzyloxy-5-fluorophenyl) -2-hydroxybutyric acid (5.34 g). This acid was dissolved in diisopropyl ether (320 ml) and (−)-phenethylamine (2.13 g) was added. The solution was stored at ambient temperature for 75 hours. The precipitate (5.8 g) was filtered off. This salt was recrystallised from a mixture of ethanol (20 ml) and diisopropyl ether (500 ml). The precipitate (2.71 g) was filtered off, dissolved in 2N aqueous hydrochloric acid solution and extracted with diethyl ether. The organic phase was washed with a saturated aqueous sodium chloride solution, dried (MgSO4) and evaporated to give (+)-2-(3-benzyloxy-5-fluorophenyl) -2-hydroxybutyric acid (1.86 g).

A solution of diazomethane in diethyl ether was added to a solution of (−)-2-(3-benzyloxy-5-fluorophenyl) 2-hydroxybutyric acid (2.24 g) in diethyl ether (35 ml) until the reaction mixture retained a yellow colouration. The mixture was evaporated to give methyl (−)-2-(3-benzyloxy-5-fluorophenyl)-2-hydroxybutyrate (2.27 g).

Lithium aluminium hydride (0.345 g) was added to a solution of the ester so obtained in diethyl ether (70 ml) and the mixture was stirred at ambient temperature for 1 hour. Water (10 ml) was added dropwise and the mixture was filtered. The organic layer was dried (MgSO4) and evaporated to give (−)-2-(3-benzyloxy-5-fluorophenyl)butane-1,2-diol (2.2 g), as an oil.

Using the procedure described in Example 1, the diol so obtained was reacted with acetone to give (−)-4-(3-benzyloxy 5-fluorophenyl)-4-ethyl-2,2-dimethyl -1,3 dioxolane (2.27 g), $[\alpha]^{20}$ −13.4°.

Using the procedure described In the third paragraph of the portion of Example 6 which is concerned with the preparation of starting materials, the product so obtained was hydrogenolysed to give (−)-4-ethyl-4-(5-fluoro-3-hydroxyphenyl) -2,2-dimethyl-1,3-dioxolane (0.36 g), as an oil.

Using the procedure described in the four paragraphs immediately above, (+)-2-(3-benzyloxy-5-fluorophenyl) -2-hydroxybutyric acid was converted into (+)-4-ethyl-4-(5-fluoro-3-hydroxyphenyl)-2,2-dimethyl-1,3-dioxolane in 90% yield.

EXAMPLE 22

Using the procedure described in Example 6, (−)-4-ethyl-4-(5-fluoro-3-hydroxyphenyl)-2,2-dimethyl -1,3-dioxolane was reacted with 2-bromomethyl-7-fluoronaphthalene. There was thus obtained (−)-4-ethyl-4-[5-fluoro-3-(7-fluoronaphth-2-ylmethoxy)phenyl-2,2-dimethyl-1,3-dioxolane in 82% yield, m p. 53°–54° C., $[\alpha]^{20}$ = −12° (chloroform, c=0.75 g/100 ml).

EXAMPLE 23

A mixture of 2-hydroxy-2-[3-(naphth-2-ylmethoxy)-phenylbutanethiol (1.35 g), acetone (40 ml) and concentrated sulphuric acid (23 drops) was stirred at ambient temperature for 16 hours. The mixture was partitioned between diethyl ether and a saturated aqueous sodium bicarbonate solution. The organic phase was washed with a saturated aqueous sodium chloride solution, dried (MgSO4) and evaporated. The residue was purified by column chromatography using a 1:1 v/v mixture of petroleum ether and methylene chloride as eluent. There was thus obtained 5-ethyl -2,2-dimethyl-5-3-(naphth-2-ylmethoxy)phenyl -1,3-oxathiolane (0.8 g, 53%), m.p. 95°–96° C.

The 2-hydroxy-2-[3-(naphth-2-ylmethoxy)phenyl-butanethiol, used as a starting material, was obtained as follows:

Trimethylsulphoxonium iodide (1.06 g) was added portionwise to a stirred suspension of sodium hydride (50% w/w dispersion in mineral oil; 0.21 g) in dimethylsulphoxide (7 ml) and the mixture was stirred at ambient temperature for 30 minutes. 3-(Naphth-2-ylmethoxy)-propiophenone (1.16 g) was added and the mixture was stirred at ambient temperature for 1 hour. The mixture was partitioned between diethyl ether and cold water. The organic phase was washed with a saturated aqueous sodium chloride solution, dried (MgSO4) and evaporated. The residue was triturated in a mixture of hexane and diethyl ether. There was thus obtained 2-ethyl-2-[3-(naphth-2-ylmethoxy)phenyl]oxirane (0.8 g, 67%), m.p. 80° C.

After repetition of the above reaction, N-benzyl-trimethylammonium hydroxide (0.4 ml of a 40% w/v solution in methanol) was added to a solution of the product so obtained (1.22 g) in methanol (40 ml) which had been saturated with hydrogen sulphide gas and the mixture was heated to 45° C. for 4.5 hours. The mixture was acidified by the addition of 2N aqueous hydrochloric acid solution and evaporated. The residue was partitioned between diethyl ether and water. The organic phase was washed with a saturated aqueous sodium chloride solution, dried (MgSO4) and evaporated to give the required starting material (1.35 g), as an oil which was stored under an atmosphere of nitrogen to prevent oxidation.

EXAMPLE 24

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/w paste) | 2.25 |
| Magnesium stearate | 3.0 |

| (c) Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 mg |
| Lactose Ph. Eur | 488.5 |
| Magnesium stearate | 1.5 |

| (e) Injection I | (50 mg/ml) |
|---|---|
| Compound X | 5.0% w/v |
| 1 M Sodium hydroxide solution | 15.0% v/v |
| 0.1 M Hydrochloric acid (to adjust pH to 7.6) | 4.5% w/v |
| Polyethylene glycol 400 | |
| Water for injection to 100% | |

| (f) Injection II | (10 mg/ml) |
|---|---|
| Compound X | 1.0% w/v |
| Sodium phosphate BP | 3.6% w/v |
| 0.1 M Sodium hydroxide solution | 15.0% v/v |
| Water for injection to 100% | |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |

-continued

| | | |
|---|---|---|
| Water for injection to 100% | | |
| (h) Aerosol I | | mg/ml |
| Compound X | | 10.0 |
| Sorbitan trioleate | | 13.5 |
| Trichlorofluoromethane | | 910.0 |
| Dichlorodifluoromethane | | 490.0 |
| (i) Aerosol II | | mg/ml |
| Compound X | | 0.2 |
| Sorbitan trioleate | | 0.27 |
| Trichlorofluoromethane | | 70.0 |
| Dichlorodifluoromethane | | 280.0 |
| Dichlorotetrafluoroethane | | 1094.0 |
| (j) Aerosol III | | mg/ml |
| Compound X | | 2.5 |
| Sorbitan trioleate | | 3.38 |
| Trichlorofluoromethane | | 67.5 |
| Dichlorodifluoromethane | | 1086.0 |
| Dichlorotetrafluoroethane | | 191.6 |
| (k) Aerosol IV | | mg/ml |
| Compound X | | 2.5 |
| Soya lecithin | | 2.7 |
| Trichlorofluoromethane | | 67.5 |
| Dichlorodifluoromethane | | 1086.0 |
| Dichlorotetrafluoroethane | | 191.6 |

Note

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE $$Ar^1-A^1-O-Ar^2-\underset{\underset{R^3}{|}}{\overset{\overset{OR^1}{|}}{C}}-R^2 \qquad I$$

$$HO-Ar^2-\underset{\underset{R^3}{|}}{\overset{\overset{O-A^2}{|}}{C}}\diagdown_{A^3}^{X} \qquad II$$

$$R^4-O-Ar^2-\underset{\underset{R^3}{|}}{\overset{\overset{O-A^2}{|}}{C}}\diagdown_{A^3}^{X} \qquad III$$

$$R^4-O-Ar^2-\underset{\underset{R^3}{|}}{\overset{\overset{OH}{|}}{C}}-A^3-X-R^5 \qquad IV$$

$$R^4-O-Ar^2-\underset{\underset{R^3}{|}}{\overset{\overset{OH}{|}}{C}}-A^3-XH \qquad V$$

-continued

CHEMICAL FORMULAE

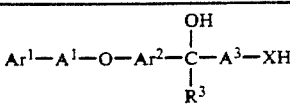

$$Ar^1-A^1-O-Ar^2-\underset{\underset{R^3}{|}}{\overset{\overset{OH}{|}}{C}}-A^3-XH \qquad VI$$

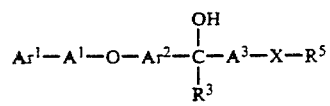

$$Ar^1-A^1-O-Ar^2-\underset{\underset{R^3}{|}}{\overset{\overset{OH}{|}}{C}}-A^3-X-R^5 \qquad VII$$

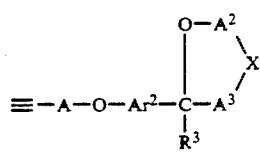

$$\equiv-A-O-Ar^2-\underset{\underset{R^3}{|}}{\overset{\overset{O-A^2}{|}}{C}}\diagdown_{A^3}^{X} \qquad VIII$$

What we claim is:

1. A cyclic ether derivative of the formula I

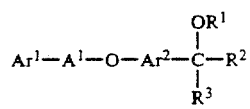

$$Ar^1-A^1-O-Ar^2-\underset{\underset{R^3}{|}}{\overset{\overset{OR^1}{|}}{C}}-R^2 \qquad I$$

wherein

Ar$^1$ is phenyl or naphthyl which may optionally bear one or more substituents selected from halogeno, hydroxy, carboxy, cyano, (1-4C)alkyl, (2-4C)alkenyl, (2-4C)alkynyl, (1-4C)alkoxy, (1-4C)alkylthio, (1-4C)alkylsulphinyl, (1-4C)alkylsulphonyl, (1-4C)alkylamino, di-[(1-4C)alkyl]amino, (1-4C)alkoxycarbonyl, (2-4C)alkanoyl, hydroxy-(1-4C)alkyl, fluoro-(1-4C)alkyl and cyano-(1-4C)alkoxy;

wherein A$^1$ is (1-6C)alkylene, (3-6C)alkenylene, (3-6C)alkynylene or cyclo(3-6C)alkylene;

wherein Ar$^2$ is phenylene which may optionally bear one or two substituents selected from halogeno, hydroxy, amino, nitro, cyano, carbamoyl, (1-4C)alkyl, (3-4C)alkenyloxy, (1-4C)alkoxy, (1-4C)alkylthio, (1-4C)alkylsulphinyl, (1-4C)alkylsulphonyl, (1-4C)alkylamino, di-[(1-4C)alkyl]amino, fluoro-(1-4C)alkyl, (1-4C)alkoxycarbonyl, N-[(1-4C)alkyl]carbamoyl, N,N-di-[(1-4C)alkylcarbamoyl, (2-4C)alkanoylamino, cyano-(1-4C)alkoxy, carbamoyl-(1-4C)alkoxy and (1-4C)alkoxycarbonyl-(1-4C)alkoxy;

wherein R$^1$ and R$^2$ together form a group of the formula —A$^2$—X—A$^3$— which, together with the oxygen atom to which A$^2$ is attached and with the carbon atom to which A$^3$ is attached, defines a ring having 5 to 7 ring atoms, wherein A$^2$ and A$^3$, which may be the same or different, each is (1-6C)alkylene, cyclopentylidene or cyclohexylidene and X is oxy, and which ring may bear one or two substituents, which may be the same or different, selected from hydroxy, (1-4C)alkoxy, hydroxy-(1-4C)alkyl and (1-4C)alkoxy-(1-4C)alkyl; and wherein R$^3$ is (1-6C)alkyl, (2-6C)alkenyl, (2-6C)alkynyl, fluoro-(1-4C)alkyl, cyano-(1-4C)alkyl, hydroxy-(1-4C)alkyl, (1-4C)alkoxy-(1-4C)alkyl, (2-4C)alkanoyloxy(1-4C)alkyl or (2-4C)alkanoyl-(1-4C)alkyl; or a pharmaceutically-acceptable salt thereof.

2. A cyclic ether derivative of the formula I as claimed in claim 1 wherein
Ar$^1$ is phenyl, naphth-1-yl or naphth-2-yl which may optionally bear one or two substituents selected from fluoro, chloro, cyano, methyl, methoxy, difluoromethyl and trifluoromethyl;
A$^1$ is methylene, 1-propenylene or 1-propynylene;
Ar$^2$ is 1,3-phenylene or 1,4-phenylene which may optionally bear one substituent selected from hydroxy, amino, nitro, methoxy, methylamino, cyanomethoxy and trifluoromethyl;
R$^1$ and R$^2$ together form a group of the formula —A$^2$—X—A$^3$— which, together with the oxygen atom to which A$^2$ is attached and with the carbon atom to which A$^3$ is attached, defines a ring having 5 ring atoms, wherein A$^2$ is methylene, ethylidene, or isopropylidene, A$^3$ is methylene and X is oxy, and R$^3$ is methyl or ethyl; or a pharmaceutically-acceptable salt thereof.

3. A cyclic ether derivative of the formula I as claimed in claim 1 wherein
Ar$^1$ is phenyl or naphth-2-yl which may optionally bear one or two substituents selected from fluoro, chloro, bromo, methyl, ethyl, propyl, tert-butyl and trifluoromethyl;
A$^1$ is methylene or 1-propynylene;
Ar$^2$ is 1,3-phenylene or 1,4-phenylene which may optionally bear one substituent selected from fluoro, amino, methoxy and trifluoromethyl;
R$^1$ and R$^2$ together form a group of the formula —A$^2$—X—A$^3$— which, together with the oxygen atom to which A$^2$ is attached and with the carbon atom to which A$^3$ is attached, defines a ring having 5 ring atoms, wherein A$^2$ is methylene, ethylidene, propylidene, isopropylidene, butylidene, isobutylidene, sec-butylidene, pentan-2-ylidene, pentan-3-ylidene or cyclopentylidene, A$^3$ is methylene or ethylidene and X is oxy, and which ring may bear one substituent selected from hydroxymethyl, methoxymethyl and 2-methoxyethyl; and R$^3$ is methyl, ethyl, allyl or 2-acetylethyl;
or a pharmaceutically-acceptable salt thereof.

4. A cyclic ether derivative of the formula I as claimed in claim 1 wherein
Ar$^1$ is phenyl or naphth-2-yl which may optionally bear one substituent selected from fluoro, methyl and trifluoromethyl;
A$^1$ is methylene or 1-propynylene;
Ar$^2$ is 1,3-phenylene or 1,4-phenylene which may optionally bear one substituent selected from fluoro, methoxy and trifluoromethyl;
R$^1$ and R$^2$ together form a group of the formula —A$^2$—X—A$^3$— which, together with the oxygen atom to which A$^2$ is attached and with the carbon atom to which A$^3$ is attached, defines a ring having 5 ring atoms, wherein A$^2$ is propylidene, isopropylidene, isobutylidene, sec-butylidene and pentan-2-ylidene, A$^3$ is methylene or ethylidene and X is oxy, and R$^3$ is methyl or ethyl;
or a pharmaceutically-acceptable salt thereof.

5. A cyclic ether derivative of the formula I as claimed in claim 1 wherein
Ar$^1$ is naphth-2-yl or 7-fluoronaphth-2-yl;
A$^1$ is methylene;
Ar$^2$ is 1,3-phenylene or 5-fluoro-1,3-phenylene;
R$^1$ and R$^2$ together form a group of the formula —A$^2$—X—A$^3$— which, together with the oxygen atom to which A$^2$ is attached and with the carbon atom to which A$^3$ is attached, defines a ring having 5 ring atoms, wherein A$^2$ is isopropylidene, sec-butylidene or pentan-2-ylidene, A$^3$ is methylene or ethylidene and X is oxy, and R$^3$ is methyl or ethyl;
or a pharmaceutically-acceptable salt thereof.

6. A cyclic ether derivative of the formula I as claimed in claim 1 wherein
Ar$^1$ is naphth-2-yl; A$^1$ is methylene;
Ar2 is 1,3-phenylene;
R$^1$ and R$^2$ together form a group of the formula —A$^2$—X—A$^3$— which, together with the oxygen atom to which A$^2$ is attached and with the carbon atom to which A$^3$ is attached, defines a ring having 5 ring atoms, wherein A$^2$ is isopropylidene, A$^3$ is methylene and X is oxy, and R$^3$ is ethyl;
or a pharmaceutically-acceptable salt thereof.

7. A cyclic ether derivative of the formula I, or a pharmaceutically-acceptable salt thereof, as claimed in claim 1 selected from the group consisting of:
4-ethyl-2,2-dimethyl-4-[3-(naphth-2-ylmethoxy)phenyl]-1,3-dioxolane,
2,2,4-trimethyl-4-[3-(naphth-2-ylmethoxy)phenyl]-1,3-dioxolane,
(4RS,5RS)-2,2,4,5-tetramethyl-4-5-fluoro-3-(naphth-2-ylmethoxy)phenyl]-1,3-dioxolane,
2,4-diethyl-2-methyl-4-[3-naphth-2-ylmethoxy)phenyl-1,3 dioxolane,
4-ethyl-4-5-fluoro-3-(7-fluoronaphth -2-ylmethoxy)-phenyl]-2,2-dimethyl-1,3-dioxolane,
4-ethyl-2-methyl-4-[3-(naphth-2-ylmethoxy)phenyl]-2-propyl-1,3-dioxolane,
2,4-diethyl-4-[5-fluoro-3-(7-fluoronaphth-2-ylmethoxy)-phenyl]-2,4-dimethyl-2-propyl-1,3-dioxolane and
(+)-4-3-(7-fluoronaphth-2-ylmethoxy)phenyl]-2,4-dimethyl-2-propyl-1,3-dioxolane.

8. A pharmaceutical composition suitable in use for providing inhibition of 5-lipoxygenase which comprises an effective amount of a cyclic ether derivative of the formula I, or a pharmaceutically-acceptable salt thereof, as claimed in any one of claims 1 to 7 in association with a pharmaceutically-acceptable diluent or carrier.

9. A method of treating a disease or medical condition mediated alone or in part by one or more leukotrienes which comprises administering to a warm-blooded animal requiring such treatment a 5-lipoxygenese-inhibitory amount of a cyclic ether derivative of the formula I, or a pharmaceutically-acceptable salt thereof, as claimed in any one of claims 1 to 7.

* * * * *